(12) United States Patent
Bell et al.

(10) Patent No.: US 12,163,179 B2
(45) Date of Patent: *Dec. 10, 2024

(54) METHODS AND SYSTEMS TO MINIMIZE BARCODE EXCHANGE

(71) Applicant: 10X GENOMICS, INC., Pleasanton, CA (US)

(72) Inventors: Jason Bell, Palo Alto, CA (US); Josephine Lee, Hayward, CA (US); Corey Nemec, Fremont, CA (US); Francesca Meschi, Menlo Park, CA (US)

(73) Assignee: 10X GEMOMICS, INC., Pleasanton, CA (US)

( * ) Notice: Subject to any disclaimer, the term of this patent is extended or adjusted under 35 U.S.C. 154(b) by 278 days.

This patent is subject to a terminal disclaimer.

(21) Appl. No.: 16/530,930

(22) Filed: Aug. 2, 2019

(65) Prior Publication Data

US 2020/0263232 A1  Aug. 20, 2020

Related U.S. Application Data

(60) Provisional application No. 62/714,476, filed on Aug. 3, 2018.

(51) Int. Cl.
*C12Q 1/6806* (2018.01)
*C12N 9/12* (2006.01)
*C12N 15/10* (2006.01)

(52) U.S. Cl.
CPC ......... *C12Q 1/6806* (2013.01); *C12N 9/1241* (2013.01); *C12N 15/1093* (2013.01); *C12N 2310/333* (2013.01); *C12N 2310/334* (2013.01); *C12N 2310/335* (2013.01); *C12N 2310/336* (2013.01); *C12Q 2563/149* (2013.01); *C12Q 2563/185* (2013.01); *C12Y 302/02027* (2013.01)

(58) Field of Classification Search
CPC ........ C12Q 2525/186; C12Q 2525/119; C12Q 2563/149; C12Q 1/6806; C12Q 2563/179; C12Q 2525/121; C12Q 2565/519; C12Q 2525/301; C12N 15/1093; C12N 2310/333; C12N 2310/334; C12N 2310/335; C12N 2310/336

See application file for complete search history.

(56) References Cited

U.S. PATENT DOCUMENTS

| | | |
|---|---|---|
| 4,124,638 A | 11/1978 | Hansen |
| 5,137,829 A | 8/1992 | Nag et al. |
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,965,443 A | 10/1999 | Reznikoff et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,207,384 B1 | 3/2001 | Mekalanos et al. |
| 6,294,385 B1 | 9/2001 | Goryshin et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |

(Continued)

FOREIGN PATENT DOCUMENTS

| | | |
|---|---|---|
| CN | 106795553 A | 5/2017 |
| EP | 1019496 B1 | 9/2004 |

(Continued)

OTHER PUBLICATIONS

Lan et al., "Single-cell genome sequencing at ultra-high-throughput with microfluidic droplet barcoding," Nature Biotechnology, published on-line May, vol. 35, No. 7, pp. 640-646 (Year: 2017).*
Maroney et al., "Direct detection of small RNAs using splinted ligation," Nature Protocols, vol. 3, No. 2, pp. 279-287. (Year: 2008).*
Klein et al., "InDrops and Drop-seq technologies for single-cell sequencing," Lab Chip, vol. 17, pp. 2540-2541. (Year: 2017).*
Zilionis et al., "Single-cell barcoding and sequencing using droplet microfluidics," vol. 12, No. 1, pp. 44-73. (Year: 2017).*
Abate, A.R. et al. "Beating Poisson encapsulation statistics using close-packed ordering" Lab on a Chip (Sep. 21, 2009) 9(18):2628-2631.
Ackermann, et al. Integration of ATAC-seq and RNA-seq identifies human alpha cell and beta cell signature genes. Mol Metab. Jan. 11, 2016;5(3):233-244. doi: 10.1016/j.molmet.2016.01.002. eCollection Mar. 2016.

(Continued)

*Primary Examiner* — Young J Kim
(74) *Attorney, Agent, or Firm* — Wilson Sonsini Goodrich & Rosati

(57) ABSTRACT

Methods and compositions to minimize barcode exchange during the preparation of barcoded next-generation sequencing libraries prepared from a single cell. The methods utilize oligonucleotides containing a 3'-terminated blocking group or sequences that prevent amplification or extension.

30 Claims, 22 Drawing Sheets

Specification includes a Sequence Listing.

(56) References Cited

U.S. PATENT DOCUMENTS

| | | |
|---|---|---|
| 7,294,503 B2 | 11/2007 | Quake et al. |
| 7,323,305 B2 | 1/2008 | Leamon et al. |
| 7,544,473 B2 | 6/2009 | Brenner |
| 7,608,434 B2 | 10/2009 | Reznikoff et al. |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,574,847 B2 | 11/2013 | Becker et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 9,005,935 B2 | 4/2015 | Belyaev |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,080,211 B2 | 7/2015 | Grunenwald et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,238,671 B2 | 1/2016 | Goryshin et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,822,396 B2 | 11/2017 | Litterst et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,590,244 B2 | 3/2020 | Delaney et al. |
| 10,725,027 B2* | 7/2020 | Bell ............... C12Q 1/6804 |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,952,626 B2 | 4/2024 | Pfeiffer et al. |
| 2002/0005354 A1 | 1/2002 | Spence et al. |
| 2002/0051971 A1 | 5/2002 | Stuelpnagel et al. |
| 2002/0058332 A1 | 5/2002 | Quake et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2004/0068019 A1 | 4/2004 | Higuchi et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0088327 A1 | 4/2009 | Rigatti et al. |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2009/0325172 A1 | 12/2009 | Milton et al. |
| 2010/0028885 A1 | 2/2010 | Balasubramanian et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |

(56) References Cited

U.S. PATENT DOCUMENTS

| | | |
|---|---|---|
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0190032 A1 | 7/2012 | Ness et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0093916 A1 | 4/2014 | Belyaev |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0066385 A1 | 3/2015 | Schnall-Levin et al. |
| 2015/0111788 A1 | 4/2015 | Fernandez et al. |
| 2015/0220532 A1 | 8/2015 | Wong |
| 2015/0267191 A1 | 9/2015 | Steelman et al. |
| 2015/0275289 A1 | 10/2015 | Otwinowski et al. |
| 2015/0291942 A1 | 10/2015 | Gloeckner et al. |
| 2015/0292988 A1 | 10/2015 | Bharadwaj et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0208323 A1 | 7/2016 | Bernstein et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2016/0362724 A1 | 12/2016 | Bailey et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2017/0362587 A1 | 12/2017 | Hindson et al. |
| 2018/0030515 A1 | 2/2018 | Regev et al. |
| 2018/0051322 A1 | 2/2018 | Church et al. |
| 2018/0071695 A1 | 3/2018 | Weitz et al. |
| 2018/0080075 A1 | 3/2018 | Brenner et al. |
| 2018/0105808 A1 | 4/2018 | Mikkelsen et al. |
| 2018/0195112 A1 | 7/2018 | Lebofsky et al. |
| 2018/0216162 A1 | 8/2018 | Belhocine et al. |
| 2018/0312822 A1 | 11/2018 | Lee et al. |
| 2018/0312873 A1 | 11/2018 | Zheng |
| 2018/0334670 A1 | 11/2018 | Bharadwaj et al. |
| 2018/0340169 A1 | 11/2018 | Belhocine et al. |
| 2018/0355348 A1 | 12/2018 | Adey et al. |
| 2018/0371545 A1 | 12/2018 | Wong et al. |
| 2019/0002967 A1 | 1/2019 | Chen et al. |
| 2019/0032128 A1 | 1/2019 | Chen et al. |
| 2019/0040382 A1 | 2/2019 | Steemers et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0085391 A1 | 3/2019 | Hindson et al. |
| 2019/0100632 A1 | 4/2019 | Delaney et al. |
| 2019/0127731 A1 | 5/2019 | McDermott |
| 2019/0134633 A1 | 5/2019 | Bharadwaj et al. |
| 2019/0136316 A1 | 5/2019 | Hindson et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0249226 A1 | 8/2019 | Bent et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2021/0115595 A1* | 4/2021 | Drmanac ............ C12N 15/1082 |
| 2021/0190770 A1 | 6/2021 | Delaney et al. |
| 2021/0213413 A1* | 7/2021 | Saligrama ............ C12Q 1/6874 |
| 2021/0270703 A1 | 9/2021 | Abousoud |
| 2024/0002914 A1 | 1/2024 | Pfeiffer et al. |

FOREIGN PATENT DOCUMENTS

| | | |
|---|---|---|
| EP | 1841879 A2 | 10/2007 |
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009147386 A1 | 12/2009 |
| WO | WO-2009152928 A2 | 12/2009 |

(56) References Cited

FOREIGN PATENT DOCUMENTS

| | | |
|---|---|---|
| WO | WO-2010033200 A2 | 3/2010 |
| WO | WO-2010048605 A1 | 4/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015074017 A1 | 5/2015 |
| WO | WO-2015164212 A1 | 10/2015 |
| WO | WO-2016040476 A1 | 3/2016 |
| WO | WO-2016061517 A1 | 4/2016 |
| WO | WO-2016126871 A2 | 8/2016 |
| WO | WO-2016168584 A1 | 10/2016 |
| WO | WO-2016191618 A1 | 12/2016 |
| WO | WO-2016207647 A1 | 12/2016 |
| WO | WO-2016207653 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017066231 A1 | 4/2017 |
| WO | WO-2017075265 A1 | 5/2017 |
| WO | WO-2017079406 A1 | 5/2017 |
| WO | WO-2017180949 A1 | 10/2017 |
| WO | WO-2017184707 A1 | 10/2017 |
| WO | WO-2017197343 A2 | 11/2017 |
| WO | WO-2018031631 A1 | 2/2018 |
| WO | WO-2018039338 A1 | 3/2018 |
| WO | WO-2018039969 A1 | 3/2018 |
| WO | WO-2018075693 A1 | 4/2018 |
| WO | WO-2018091676 A1 | 5/2018 |
| WO | WO-2018103025 A1 | 6/2018 |
| WO | WO-2018119301 A1 | 6/2018 |
| WO | WO-2018119447 A2 | 6/2018 |
| WO | WO-2018129368 A1 | 7/2018 |
| WO | WO-2018172726 A1 | 9/2018 |
| WO | WO-2018191701 A1 | 10/2018 |
| WO | WO-2018213643 A1 | 11/2018 |
| WO | WO-2018217912 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019060907 A1 | 3/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

Adamson et al., "Production of arrays of chemically distinct nanolitre plugs via repeated splitting in microfluidic devices", Lab Chip 6(9): 1178-1186 (Sep. 2006).

Adey, et al. Rapid, low-input, low-bias construction of shotgun fragment libraries by high-density in vitro transposition. Genome Biology 11:R119 (2010).

Adey, et al., "Ultra-low-input, tagmentation-based whole-genome bisulfite sequencing", Genome Research, 2012, 22 ;6): 1139-1143.

Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna et al.: Formation of dispersions using "flow focusing" in microchannels: Applied Physics Letters, vol. 82, No. 3, pp. 364-366 (2003).

Ason et al. DNA sequence bias during Tn5 transposition. Journal of molecular biology 335.5 (2004): 1213-1225.

Baret, "Surfactants in droplet-based microfluidics" Lab Chip (12(3):422-433 (2012).

Beer et al. On-Chip, Real-Time, Single-Copy Polymerase Chain Reaction in Picoliter Droplets. Anal Chem 79:8471-8475 (2007).

Berkum, et al. Hi-C: a method to study the three-dimensional architecture of genomes. J Vis Exp. May 6, 2010;(39). pii: 1869. doi: 10.3791/1869.

Boyle, et al. "High-resolution genome-wide in vivo footprinting of diverse transcription factors in human cells", Genome Res. Mar. 2011;21(3):456-64.

Braeckmans et al., Scanning the Code. Modern Drug Discovery. 2003:28-32.

Brenner, et al. "In vitro cloning of complex mixtures of DNA on microbeads: physical separation of differentially expressed cDNAs." Proc Natl Acad Sci U S A. Feb. 15, 2000;97(4):1665-70.

Buchman GQ, et al. Selective RNA amplification: a novel method using dUMP-containing primers and uracil DNA glycosylase. PCR Methods Appl. Aug. 1993; 3(1):28-31.

Buenrostro, et al. ATAC-seq: A Method for Assaying Chromatin Accessibility Genome-Wide. Curr Protoc Mol Biol. Jan. 5, 2015;109: 21.29.1-21.29.9. doi: 10.1002/0471142727.mb2129s109.

Buenrostro, et al. Single-cell chromatin accessibility reveals principles of regulatory variation. Nature. Jul. 23, 2015;523(7561):486-90. doi: 10.1038/nature14590. Epub Jun. 17, 2015.

Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.

(56) References Cited

OTHER PUBLICATIONS

Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Cao, et al. Joint profiling of chromatin accessibility and gene expression in thousands of single cells. Science. Sep. 28, 2018;361(6409):1380-1385. doi: 10.1126/science.aau0730. Epub Aug. 30, 2018.
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chen et al. High-throughput sequencing of the transcriptome and chromatin accessibility in the same cell. Nat Biotechnol. Oct. 14, 2019. doi: 10.1038/s41587-019-0290-0. [Epub ahead of print].
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,102, filed Jun. 6, 2019.
Costello, et al. Characterization and remediation of sample index swaps by non-redundant dual indexing on massively parallel sequencing platforms. BMC Genomics. 2018; 19: 332. Published online May 8, 2018. doi: 10.1186/s12864-018-4703-0.
Craig. Unity in Transposition Reactions. Science. Oct. 13, 1995;270(5234):253-4.
Cusanovich, et al. A Single-Cell Atlas of In Vivo Mammalian Chromatin Accessibility. Cell. Aug. 23, 2018;174(5):1309-1324.e18. doi: 10.1016/j.cell.2018.06.052. Epub Aug. 2, 2018.
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dekker, et al. Capturing chromosome conformation. Science. Feb. 15, 2002;295(5558):1306-11.
Drmanac et al., Sequencing by hybridization (SBH): advantages, achievements, and opportunities. Adv Biochem Eng Biotechnol. 2002;77 :75-101.
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Epicentre., "EZ-Tn5TM Custom Transposome Construction Kits", http://www.epicentre.com, pp. 1-17, 2012.
Esser-Kahn, et al. Triggered release from polymer capsules. Macromolecules. 2011; 44:5539-5553.
Gaiti, et al. Epigenetic evolution and lineage histories of chronic lymphocytic leukaemia. Nature. May 2019; 569(7757):576-580. doi: 10.1038/s41586-019-1198-z. Epub May 15, 2019.
Gangadharan et al., DNA transposon Hermes insert into DNA in nucleosome-free regions in vivo, Proc nat Ad Sci, Dec. 21, 2010, vol. 107, No. 51, pp. 1966-1972.

Gaublomme, et al. Nuclei multiplexing with barcoded antibodies for single-nucleus genomics. Nat Commun. Jul. 2, 2019;10(1):2907. doi: 10.1038/s41467-019-10756-2.
Gericke, et al. Functional cellulose beads: preparation, characterization, and applications. Chemical reviews 113.7 (2013): 4812-4836.
Gravina, et al. Single-cell genome-wide bisulfite sequencing uncovers extensive heterogeneity in the mouse liver methylome. Genome Biol. Jul. 5, 2016;17(1):150. doi: 10.1186/s13059-016-1011-3.
Gravina, et al. Single-cell, locus-specific bisulfite sequencing (SLBS) for direct detection of epimutations in DNA methylation patterns. Nucleic Acids Res. Aug. 18, 2015;43(14):e93. doi: 10.1093/nar/gkv366. Epub Apr. 19, 2015.
Green et al. Insertion site preference of Mu, Tn5, and Tn7 transposons. Mobile DNA 3.1 (2012): 3.
Greenleaf, et al. Assaying the epigenome in limited Nos. of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(suppl5):4742.
Jia, et al. Single cell RNA-seq and ATAC-seq analysis of cardiac progenitor cell transition states and lineage settlement. Nat Commun. Nov. 19, 2018;9(1):4877. doi: 10.1038/s41467-018-07307-6.
Jin, et al. Genome-wide detection of DNase I hypersensitive sites in single cells and FFPE tissue samples. Nature. Dec. 3, 2015;528(7580):142-6. doi: 10.1038/nature15740.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kilgore, et al. Single-molecule and population probing of chromatin structure using DNA methyltransferases. Methods. Mar. 2007;41(3):320-32.
Kivioja, et al. Counting absolute Nos. of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Lagally, et al. Single-Molecular DNA Amplification and Analysis in an Integrated Microfluidic Device. Anal Chem. Feb. 1, 2001;73(3):565-70.

(56) References Cited

OTHER PUBLICATIONS

Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis By Transcriptional And Epigenetic States In Human Adult Brain". Apr. 19, 2017. doi: https://doi.org/10.1101/128520.
Lennon et al. A scalable, fully automated process for construction of sequence-ready barcoded libraries for 454. Genome Biology 11:R15 (2010).
Macconaill, et al. Unique, dual-indexed sequencing adapters with UMIs effectively eliminate index cross-talk and significantly improve sensitivity of massively parallel sequencing. BMC Genomics 19, 30, doi:10.1186/s12864-017-4428-5 (2018).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Navin. The first five years of single-cell cancer genomics and beyond. Genome Res. Oct. 2015;25(10):1499-507. doi: 10.1101/gr. 191098.115.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, R. et al., "Single cell multiplex gene detection and sequencing using microfluidicallygenerated agarose emulsions" Angew. Chem. Int. Ed. Engl. (2011) 50(2):390-395.
Orakdogen, N. "Novel responsive poly(N,N-dimethylaminoethyl methacrylate) gel beads: preparation, mechanical properties and pH-dependent swelling behavior" J Polym Res (2012) 19:9914.
Park. ChIP-seq: advantages and challenges of a maturing technology. Nature Reviews Genetics vol. 10, pp. 669-680 (2009).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ponnaluri, et al. NicE-seq: high resolution open chromatin profiling. Genome Biol. Jun. 28, 2017;18(1):122. doi: 10.1186/s13059-017-1247-6.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 17:847-850.
Ramani, et al. Massively multiplex single-cell Hi-C. Nat Methods. Mar. 2017; 14(3): 263-266. Published online Jan. 30, 2017.doi: 10.1038/nmeth.4155.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, A. et al., "High-throughput single-cell labeling (Hi-SCL) for RNA-Seq using drop-based microfluidics" PLOS One (May 22, 2015) 0116328 (14 pages).
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Schutsky, et al. APOBEC3A efficiently deaminates methylated, but not TET-oxidized, cytosine bases in DNA. Nucleic Acids Res. Jul. 27, 2017;45(13):7655-7665. doi: 10.1093/nar/gkx345.
Seiffert, et al. Microfluidic fabrication of smart microgels from macromolecular precursors. 2010. Polymer.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.
Simon, et al., "Using formaldehyde-assisted isolation of regulatory elements (FAIRE) to isolate active regulatory DNA", Nature Protocols, 2012, 7(2): 256-267.
Smallwood, et al. Single-cell genome-wide bisulfite sequencing for assessing epigenetic heterogeneity. Nat Methods. Aug. 2014; 11(8):817-820. doi: 10.1038/nmeth.3035. Epub Jul. 20, 2014.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)"107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

(56) References Cited

OTHER PUBLICATIONS

Ushijima et al, Detection and interpretation of altered methylation patterns in cancer cells, 2005, Nature reviews, 5, 223-231.
Uttamapinant, et al. Fast, cell-compatible click chemistry with copper-chelating azides for biomolecular labeling.Angew. Chem. Int. End. Engl., Jun. 11, 2012: 51(24) pp. 5852-5856.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. CoBATCH for High-Throughput Single-Cell Epigenomic Profiling. Mol Cell. Oct. 3, 2019;76(1):206-216.e7. doi: 10.1016/j.molcel.2019.07.015. Epub Aug. 27, 2019.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Xu, et al. Single-cell lineage tracing by endogenous mutations enriched in transposase accessible mitochondrial DNA. Elife. Apr. 9, 2019;8. pii: e45105. doi: 10.7554/eLife.45105.
Zentner, et al. Surveying the epigenomic landscape, one base at a time. Genome Biol. Oct. 22, 2012;13(10):250. doi: 10.1186/gb4051.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng et al. Multiplex chromatin interactions with single-molecule precision. Nature 566(7745):558-562 (Feb. 2019).
Zheng, X.Y. et al. "Haplotyping germline and cancer genomes with high-throughput linked-read sequencing" Nature Biotech (Feb. 1, 2016) 34(3):303-311.
Zhu, et al. Reverse transcriptase template switching: a SMART approach for full-length cDNA library construction. Biotechniques. Apr. 2001;30(4):892-7.
Zhu, et al. An ultra high-throughput method for single-cell joint analysis of open chromatin and transcriptome. Nat Struct Mol Biol. Nov. 2019;26(11):1063-1070. doi: 10.1038/s41594-019-0323-x. Epub Nov. 6, 2019.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
Cusanovich, et al. Multiplex single-cell profiling of chromatin accessibility by combinatorial cellular indexing. Sciencexpress. May 7, 2014. p. 1-9. doi: 10.1126/science.aab1601.
Seiffert, et al. Microfluidic fabrication of smart microgels from macromolecular precursors.Polymer. vol. 51, Issue 25, Nov. 26, 2010, pp. 5883-5889.
PCT/US2020/017785 Application filed on Feb. 11, 2020 by Ziraldo, Solongo B. et al.
PCT/US2020/017789 Application filed on Feb. 11, 2020 by Belhocine, Zahara Kamila et al.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez, Luigi Jhon Alvarado, filed Jul. 21, 2021.
Co-pending U.S. Appl. No. 17/499,039, inventors Pfeiffer; Katherine et al., filed Oct. 12, 2021.
Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Duffy et al., Rapid Protyping of Microfluidic Systems and Polydimethylsiloxane, Anal Chem 70:4974-4984 (1998).
Co-pending PCT application No. PCT/US2022/017558, inventors Dagmar et al., filed Feb. 23, 2022.
Co-pending PCT application No. PCT/US2022/017377, inventors Pfeiffer et al., filed Feb. 22, 2022.
Co-pending U.S. Appl. No. 17/318,364, inventors Bava; Felice Alessio et al., filed May 12, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/580,947, inventor Gibbons; Michael, filed Jan. 21, 2022.
Co-pending U.S. Appl. No. 17/831,835, inventor Martinez; Luigi Jhon Alvarado, filed Jun. 3, 2022.
Co-pending U.S. Appl. No. 17/957,781, inventor Bava; Felice Alessio, filed Sep. 30, 2022.
Co-pending U.S. Appl. No. 18/046,843, inventor Toh; Mckenzi, filed Oct. 14, 2022.
Co-pending U.S. Appl. No. 18/152,650, inventor Shastry; Shankar, filed Jan. 10, 2023.
Co-pending U.S. Appl. No. 18/392,684, inventors Fernandes; Sunjay Jude et al., filed Dec. 21, 2023.
Co-pending U.S. Appl. No. 18/643,684, inventor Bava; Felice Alessio, filed Apr. 23, 2024.
Co-pending U.S. Appl. No. 18/743,583, inventor Nagendran; Monica, filed Jun. 14, 2024.

\* cited by examiner

*FIG. 7*
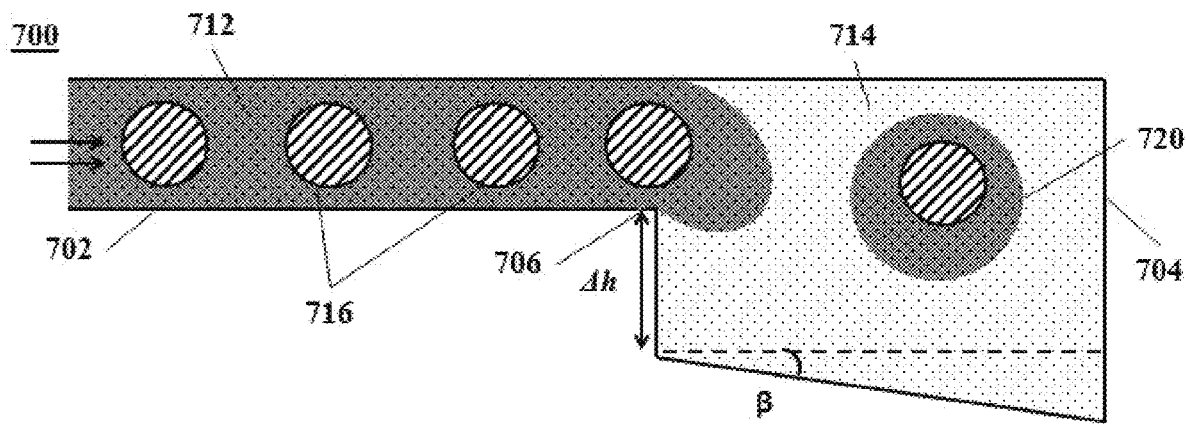
*FIG. 7A*
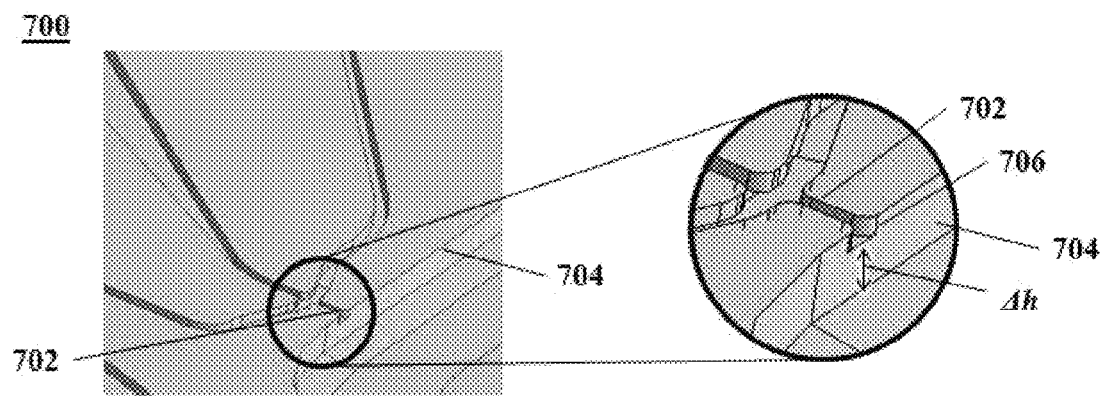
*FIG. 7B*

METHODS AND SYSTEMS TO MINIMIZE BARCODE EXCHANGE

CROSS-REFERENCE

This application claims the benefit of U.S. Provisional Patent Application No. 62/714,476, filed Aug. 3, 2018, which is entirely incorporated herein by reference.

SEQUENCE LISTING

The instant application contains a Sequence Listing which has been filed electronically in ASCII format and is hereby incorporated by reference in its entirety. Said ASCII copy, created on Apr. 20, 2020, is named 43487-814_201_SL.txt and is 4,444 bytes in size.

BACKGROUND

A sample may be processed for various purposes, such as identification of a type of moiety within the sample. The sample may be a biological sample. Biological samples may be processed, such as for detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

Certain applications may benefit from the amplification or sequencing of species obtained from single cells obtained from a much larger population. In some cases, the single cells of interest may be quite rare. Thus, there is a need for sample preparation techniques that allow sequencing of nucleic acids from single cells of interest.

SUMMARY

In an aspect, provided herein is a method for nucleic acid processing, comprising: (a) in a plurality of partitions, using nucleic acid barcode molecules from a plurality of nucleic acid barcode molecules and a plurality of nucleic acid molecules to generate a plurality of barcoded nucleic acid molecules; (b) recovering the plurality of barcoded nucleic acid molecules from the plurality of partitions, to yield a mixture comprising the plurality of nucleic acid barcode molecules and a remainder of the plurality of nucleic acid barcode molecules; (c) subsequent to (b), subjecting the mixture to conditions sufficient to couple a blocking oligonucleotide to the remainder of the plurality of nucleic acid barcode molecules, wherein the blocking oligonucleotide comprises (i) a complementary region comprising a sequence at least 75% complementary to a sequence in the remainder of the plurality of nucleic acid barcode molecules; and (ii) a 3' blocking group.

In some embodiments, the 3' blocking group is configured to prevent ligation of the remainder to a nucleic acid molecule. In some embodiments, the 3' blocking group is configured to prevent extension of the primer sequence when hybridized to a target nucleic acid molecule. In some embodiments, the plurality of partitions is a plurality of droplets. In some embodiments, the plurality of partitions is a plurality of wells. In some embodiments, the blocking oligonucleotide comprises, from 5' to 3', a first stem sequence, a loop sequence, a second stem sequence at least 75% complementary to the first stem sequence, and the complementary region. In some embodiments, the 3' blocking group is at a 3' terminus of the blocking oligonucleotide. In some embodiments, the 3' blocking group is: a 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group. In some embodiments, the 2'-5' linked nucleoside is a 3'-deoxythymidine (3'-dT) 3'-deoxycytidine (3'-dC), 3'-deoxyadenosine (3'-dA), or a 3'-deoxyguanosine (3'-dG). In some embodiments, the blocking oligonucleotide is ligated to the remainder. In some embodiments, the blocking oligonucleotide comprises a 5' phosphate group.

In another aspect, disclosed herein is a composition, comprising: a nucleic acid molecule comprising, from 5' to 3': (a) a first region comprising a barcode sequence and a primer sequence; and (b) a second region comprising (i) a sequence complementary to the primer sequence; and (ii) 3' a blocking group. In some embodiments, the 3' blocking group is at a 3' terminus of the blocking oligonucleotide. In some embodiments, the 3' blocking group is a 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group. In some embodiments, the 2'-5' linked nucleoside is a 3'-deoxythymidine (3'-dT) 3'-deoxycytidine (3'-dC), 3'-deoxyadenosine (3'-dA), or a 3'-deoxyguanosine (3'-dG). In some embodiments, the second region comprises, from 5' to 3': a first stem sequence, a loop sequence, a second stem sequence at least 75% complementary to the first stem sequence, the sequence complementary to the primer sequence, and the 3' blocking group.

In yet another aspect, disclosed herein is a method for nucleic acid processing, comprising: (a) providing a reaction mixture comprising: (i) a template nucleic acid molecule; (ii) an RNase enzyme; and (iii) a plurality of nucleic acid barcode molecules, wherein each nucleic acid barcode molecule of the plurality of nucleic acid barcode molecules comprises: (A) a common barcode sequence; (B) a sequence capable of hybridizing to a target nucleic acid; (C) at least one ribonucleotide; and (D) a 3' blocking group; (b) subjecting the reaction mixture to conditions sufficient for the template nucleic acid molecule to hybridize to a nucleic acid barcode molecule of the plurality of nucleic acid barcode molecules; (c) subjecting the reaction mixture to conditions sufficient for the RNase enzyme to degrade the ribonucleotide, thereby releasing the 3' blocking group; and (d) using the template nucleic acid molecule and the nucleic acid barcode molecule to generate a barcoded template nucleic acid molecule. In some embodiments, the 3' blocking group is configured to prevent ligation of the remainder to a nucleic acid molecule. In some embodiments, the 3' blocking group is configured to prevent extension of the primer sequence when hybridized to a target nucleic acid molecule. In some embodiments, the common barcode sequence is 5' to the at least one ribonucleotide and the 3' blocking group. In some embodiments, the 3' blocking group is at a 3' terminus of the plurality of nucleic acid barcode molecules. In some embodiments, the 3' blocking group is a 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group. In some embodiments, the 2'-5' linked nucleoside is a 3'-deoxythymidine (3'-dT) 3'-deoxycytidine (3'-dC), 3'-deoxyadenosine (3'-dA), or a 3'-deoxyguanosine (3'-dG). In some embodiments, the method further comprises co-partitioning the reaction mixture into a partition. In some embodiments, the partition is a well. In some embodiments, the partition is an aqueous droplet in an emulsion. In some embodiments, the plurality of nucleic acid barcode molecules is attached to a bead. In some embodiments, the plurality of nucleic acid barcode molecules is releasably attached to the bead. In some embodiments, the bead is a gel bead. In some embodiments, the gel bead is a degradable gel bead. In some embodiments, the degradable gel bead is degradable by a chemical stimulus. In some embodiments, the chemical stimulus is a reducing agent. In some embodiments, the reaction mixture comprises the reducing agent. In some embodiments, the RNase enzyme is an RNase H2 enzyme. In some embodiments, the barcoded template nucleic acid molecule is generated by primer extension. In some embodiments, the barcoded template nucleic acid molecule is generated by nucleic acid amplification. In some embodiments, the barcoded template nucleic acid molecule is generated by ligation. In some embodiments, prior to (b), an adapter sequence is added to the template nucleic acid molecule, and wherein the sequence capable of hybridizing to the target nucleic acid is complementary to at least a portion of the adapter sequence. In some embodiments, the adapter sequence is added to the template nucleic acid molecule by a transposase. In some embodiments, the adapter sequence comprises a sequencing primer sequence and wherein the sequence capable of hybridizing to the target nucleic acid is complementary to the sequencing primer sequence.

In another aspect, described herein is a partially double-stranded nucleic acid barcode molecule comprising: (a) a first strand comprising a (i) a complement of a primer annealing sequence and (ii) a barcode sequence; and (b) a second strand comprising a (i) a 5' overhang and (ii) an abasic site, wherein the first strand and the second strand are annealed to each other.

In some embodiments, the abasic site is in the 5' overhang. In some embodiments, the abasic site is positioned at least 3 base positions 5' of a base of the second strand annealed to a base at a 3' end of the first strand. In some embodiments, the abasic site is positioned 3, 4, 5, 6, 7, or 8 base positions 5' of a base of the second strand annealed to a base at the 3' end of the first strand. In some embodiments, the abasic site is at a position in the second strand where a base at a 3' end of the first strand would anneal if a base were present at the position. In some embodiments, the second strand comprises the primer annealing sequence. In some embodiments, the partially double-stranded nucleic acid barcode molecule is attached to a bead. In some embodiments, the bead is a gel bead.

In another aspect, disclosed herein is a partially double-stranded nucleic acid barcode molecule comprising (a) a first strand comprising a (i) a complement of a primer annealing sequence and (ii) a barcode sequence; and (b) a second strand comprising (i) DNA, (ii) a 5' overhang, and (iii) a noncanonical base, wherein the first strand and the second strand are annealed to each other.

In some embodiments, the noncanonical base is in the 5' overhang. In some embodiments, the noncanonical base is positioned at least 3 bases 5' of a base of the second strand annealed to a base at a 3' end of the first strand. In some embodiments, the noncanonical base is positioned 3, 4, 5, 6, 7, or 8 bases 5' of a base of the second strand annealed to a base at the 3' end of the first strand. In some embodiments, the noncanonical base is annealed to a base at the 3' end of the first strand. In some embodiments, the noncanonical base comprises uracil. In some embodiments, the second strand comprises the primer annealing sequence. In some embodiments, the partially double-stranded nucleic acid barcode molecule is attached to a bead. In some embodiments, the bead is a gel bead.

In another aspect, provided herein is a partially double-stranded nucleic acid barcode molecule comprising (a) a first strand comprising (i) a complement of a primer annealing sequence and (ii) a barcode sequence; and (b) a second strand comprising a 5' overhang, wherein the first strand and the second strand are annealed to each other, and wherein the second strand is configured to prevent a polymerase from synthesizing a strand using all of the 5' overhang as a template.

In some embodiments, the partially double-stranded nucleic acid barcode molecule is attached to a bead. In some embodiments, the bead is a gel bead.

In another aspect, provided herein is a partially double-stranded nucleic acid barcode molecule comprising (a) a first strand comprising (i) a complement of a primer annealing sequence and (ii) a barcode sequence; and (b) a second strand comprising a 5' overhang and a 3' end comprising a block that prevents extension of the 3' end of the second strand by an enzyme, wherein the first strand and the second strand are annealed to each other.

In some embodiments, the block comprises a C3 spacer, 2'-3'-dideoxycytosine (ddC), an inverted dT, an amino group, or a phosphate. In some embodiments, the partially double-stranded nucleic acid barcode molecule is attached to a bead. In some embodiments, the bead is a gel bead.

In an aspect, provided herein is a method of generating a partially double-stranded nucleic acid barcode molecule comprising an abasic site, the method comprising (a) providing a partially double-stranded nucleic acid barcode molecule comprising (i) a first strand comprising (A) a complement of a primer annealing sequence and (B) a barcode sequence; and (ii) a second strand comprising (A) DNA, (B) a 5' overhang, and (C) a noncanonical base, wherein the first strand and the second strand are annealed to each other; and (b) treating the partially double-stranded DNA with an agent, thereby generating an abasic site at a position of the noncanonical base.

In some embodiments, the noncanonical base is uracil. In some embodiments, the agent is uracil-DNA-glycosylase (UDG). In some embodiments, the second strand comprises the primer annealing sequence.

In another aspect, provided herein is a method for nucleic acid processing, comprising, in a plurality of partitions, generating a plurality of barcoded nucleic acid molecules using nucleic acid molecules of a plurality of nucleic acid molecules and a partially double-stranded nucleic acid barcode molecule.

In some embodiments, the generating comprises ligating a nucleic acid molecule of the plurality of nucleic acid molecules to the partially double-stranded nucleic acid barcode molecule. In some embodiments, the ligating comprises ligating the nucleic acid molecule of the plurality of nucleic acid molecules to a 3' end of the first strand of the partially double-stranded nucleic acid barcode molecule. In some embodiments, the plurality of partitions is a plurality of droplets. In some embodiments, the plurality of partitions is a plurality of wells. In some embodiments, the nucleic acid molecules are tagmented nucleic acid molecules.

In some embodiments, in each partition of the plurality of partitions, the barcode sequence of the partially double-stranded nucleic acid barcode molecule is unique, and the complement of the primer annealing sequence is common.

In another aspect, provided herein is a method of nucleic acid processing comprising, (a) in a plurality of partitions (i) annealing a 5' overhang of a second strand of a partially double-stranded nucleic acid barcode molecule to a nucleic acid molecule, wherein a first strand of the partially double-stranded nucleic acid barcode molecule comprises (A) a complement of a common primer annealing sequence and (B) a unique barcode sequence and; and (i) ligating the partially double-stranded nucleic acid barcode molecule to the nucleic acid molecule, thereby generating a barcoded nucleic acid molecule; (a) pooling the barcoded nucleic acid molecules from the plurality of partitions; (b) amplifying the barcoded nucleic acid molecules using a primer that anneals to the common primer annealing sequence, wherein a rate of barcode exchange of the barcoded nucleic acid molecules following the amplifying is less than 50%.

In some embodiments, the rate of barcode exchange is less than 10%. In some embodiments, the rate of barcode exchange is less than 1%. In some embodiments, the partially double-stranded nucleic acid barcode molecule is coupled to a bead. In some embodiments, the bead is a gel bead. In some embodiments, the plurality of partitions is a plurality of droplets. In some embodiments, the plurality of partitions is a plurality of wells. In some embodiments, the nucleic acid molecule is a tagmented nucleic acid.

Disclosed herein, in some embodiments, are methods for nucleic acid processing, comprising: (a) in a plurality of partitions, using nucleic acid barcode molecules from a plurality of nucleic acid barcode molecules and a plurality of nucleic acid molecules to generate a plurality of barcoded nucleic acid molecules; (b) recovering the plurality of barcoded nucleic acid molecules from the plurality of partitions, to yield a mixture comprising the plurality of nucleic acid barcode molecules and a remainder of the plurality of nucleic acid barcode molecules; (c) subsequent to (b), subjecting the mixture to conditions sufficient to couple a blocking oligonucleotide to the remainder of the plurality of nucleic acid barcode molecules, wherein the blocking oligonucleotide comprises: (i) a complementary region comprising a sequence at least 75% complementary to a sequence in the remainder of the plurality of nucleic acid barcode molecules; and (ii) a 3' blocking group.

In some embodiments, the 3' blocking group is configured to prevent ligation of the remainder to a nucleic acid molecule. In some embodiments, the 3' blocking group is configured to prevent extension of the primer sequence when hybridized to a target nucleic acid molecule. In some embodiments, the plurality of partitions is a plurality of droplets. In some embodiments, the plurality of partitions is a plurality of wells.

In some embodiments, the blocking oligonucleotide comprises, from 5' to 3', a first stem sequence, a loop sequence, a second stem sequence at least 75% complementary to the first stem sequence, and the complementary region. In some embodiments, the 3' blocking group is at a 3' terminus of the blocking oligonucleotide. In some embodiments, the 3' blocking group is a: 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group. In some embodiments, the 2'-5' linked nucleoside is a 3'-deoxythymidine (3'-dT), 3'-deoxycytidine (3'-dC), 3'-deoxyadenosine (3'-dA), or a 3'-deoxyguanosine (3'-dG). In some embodiments, the blocking oligonucleotide is ligated to the remainder. In some embodiments, the blocking oligonucleotide comprises a 5' phosphate group.

Also disclosed herein, in some embodiments, is a composition, comprising, from 5' to 3': (a) a first region comprising a barcode sequence and a primer sequence; and (b) a second region comprising (i) a sequence complementary to the primer sequence; and (ii) 3' a blocking group. In some embodiments, the 3' blocking group is at a 3' terminus of the blocking oligonucleotide. In some embodiments, the 3' blocking group is a 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group. In some embodiments, the second region comprises, from 5' to 3': a first stem sequence, a loop sequence, a second stem sequence at least 75% complementary to the first stem sequence, the sequence complementary to the primer sequence, and the 3' blocking group.

Also disclosed herein, in some embodiments, are methods for nucleic acid processing, comprising: (a) providing a reaction mixture comprising: (i) a template nucleic acid molecule; (ii) an RNase enzyme; and (iii) a plurality of nucleic acid barcode molecules, wherein each nucleic acid barcode molecule of the plurality of nucleic acid barcode molecules comprises: (A) a common barcode sequence; (B) a sequence capable of hybridizing to a target nucleic acid; (C) at least one ribonucleotide; and (D) a 3' blocking group; (b) subjecting the reaction mixture to conditions sufficient for the template nucleic acid molecule to hybridize to a nucleic acid barcode molecule of the plurality of nucleic acid barcode molecules; (c) subjecting the reaction mixture to conditions sufficient for the RNase enzyme to degrade the ribonucleotide, thereby releasing the 3' blocking group; and (d) using the template nucleic acid molecule and the nucleic acid barcode molecule to generate a barcoded template nucleic acid molecule.

In some embodiments, the 3' blocking group is configured to prevent ligation of the remainder to a nucleic acid molecule. In some embodiments, the 3' blocking group is configured to prevent extension of the primer sequence when hybridized to a target nucleic acid molecule. In some embodiments, the barcode sequence is 5' to the at least one ribonucleotide and the 3' blocking group.

In some embodiments, the 3' blocking group is at a 3' terminus of the plurality of nucleic acid barcode molecules. In some embodiments, the 3' blocking group is a 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group. In some embodiments, the 2'-5' linked nucleoside is a 3'-deoxythymidine (3'-dT) 3'-deoxycytidine (3'-dC), 3'-deoxyadenosine (3'-dA), or a 3'-deoxyguanosine (3'-dG).

In some embodiments, the method for nucleic acid processing further comprises co-partitioning the reaction mixture into a partition. In some embodiments, the partition is a well. In some embodiments, the partition is an aqueous droplet in an emulsion.

In some embodiments, the plurality of nucleic acid barcode molecules is attached to a bead. In some embodiments, the plurality of nucleic acid barcode molecules is releasably attached to the bead. In some embodiments, the bead is a gel bead. In some embodiments, the gel bead is a degradable gel bead. In some embodiments, the degradable gel bead is degradable by a chemical stimulus. In some embodiments, the chemical stimulus is a reducing agent. In some embodiments, the reaction mixture comprises the reducing agent.

In some embodiments, the RNase enzyme is an RNase H2 enzyme. In some embodiments, the barcoded template nucleic acid molecule is generated by primer extension. In some embodiments, the barcoded template nucleic acid is generated by nucleic acid amplification, extension, or synthesis. In some embodiments, the barcoded template nucleic acid molecule is generated by ligation.

In some embodiments, the method for nucleic acid processing further comprises adding an adapter sequence to the template nucleic acid molecule prior to (b), wherein the adapter sequence is capable of hybridizing to the target nucleic acid is complementary to at least a portion of the adapter sequence. In some embodiments, the adapter sequence is added to the template nucleic acid molecule by a transposase. In some embodiments, the adapter sequence comprises a sequencing primer sequence, wherein the sequence capable of hybridizing to the target nucleic acid is complementary to the sequencing primer sequence.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7A shows a cross-section view of another example of a microfluidic channel structure with a geometric feature for controlled partitioning. FIG. 7B shows a perspective view of the channel structure of FIG. 7A.

FIG. 14A shows an exemplary sequence of a ribonucleotide-containing barcode molecule (SEQ ID NO: 9). FIG. 14B illustrates an adapter-flanked template nucleic acid molecule bound to a ribonucleotide-containing barcode molecule attached to a solid support. FIG. 14C illustrates RNase H2-dependent cleavage of the ribonucleotide and 3' blocking group, thereby facilitating barcoding of an adapter-flanked template nucleic acid molecule.

DETAILED DESCRIPTION

Figure 1:
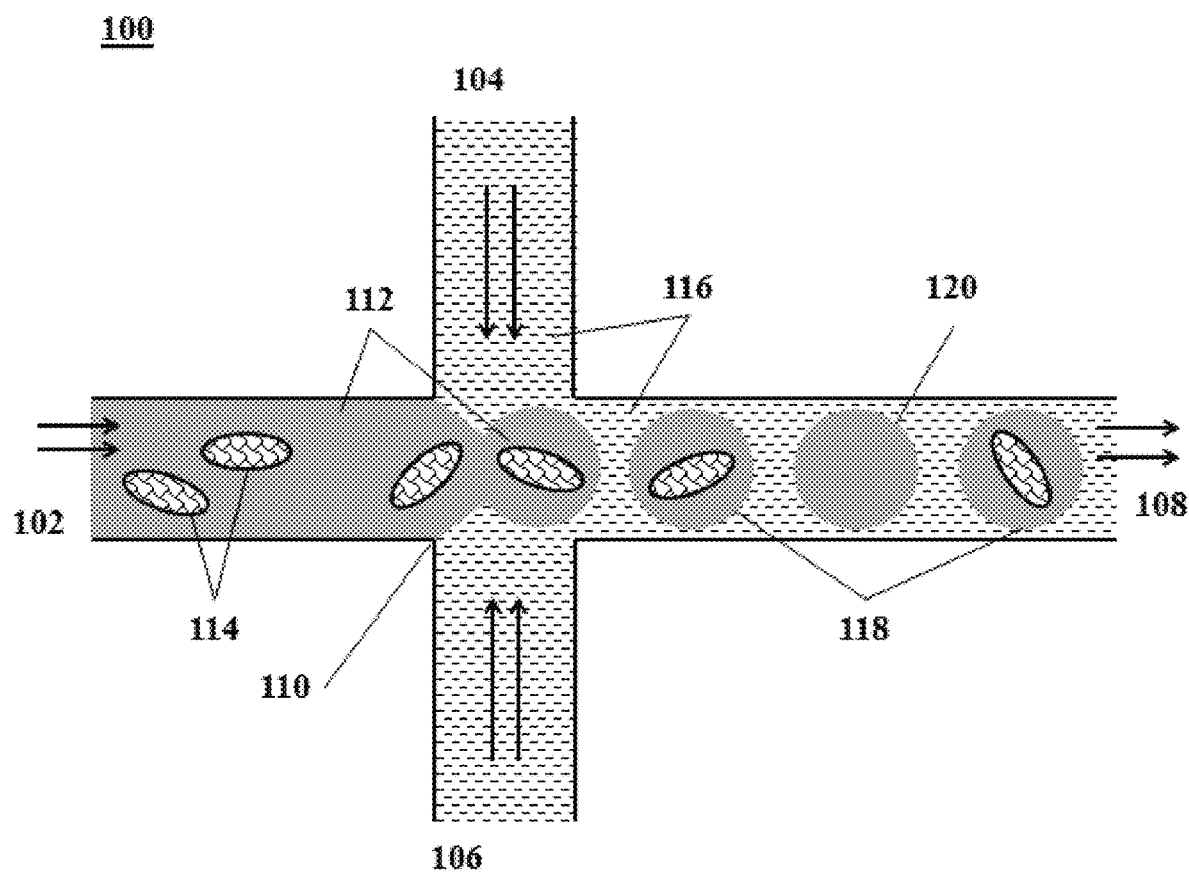
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, e.g., a mammal (e.g., human) or avian (e.g., bird), or other organism, e.g., a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules e.g., deoxyribonucleic acid (DNA) or ribonucleic acid (RNA), including variants or derivatives thereof (e.g., single stranded DNA). Sequencing can be performed by various systems currently available, e.g., without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, e.g., in random copolymers, and/or have ordered structures, e.g., in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), e.g., monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, e.g., a biopsy, core biopsy, needle aspirate, or fine needle aspirate. The sample may be a fluid sample, e.g., a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a chromosome or other portion of a genome. The biological particle may be or may include a matrix (e.g., a gel or polymer matrix) comprising a cell or one or more constituents from a cell (e.g., cell bead), e.g., DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally refers to a space or volume that may be suitable to contain one or more species or conduct one or more reactions. A partition may be a physical compartment, e.g., a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, e.g., a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, e.g., via polymerization of a droplet containing the biological particle and precursors capable of being polymerized or gelled. Unique identifiers, e.g., barcodes, may be injected into the droplets previous to, subsequent to, or concurrently with droplet generation, e.g., via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (e.g., droplets 118). A discrete droplet generated may include more than one individual biological particle 114 (not shown in FIG. 1). A discrete droplet may contain no biological particle 114 (e.g., droplet 120). Each discrete partition may maintain separation of its own contents (e.g., individual biological particle 114) from the contents of other partitions.

The second fluid 116 can comprise an oil, e.g., a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, e.g., to reduce costs and/or increase efficiency. While this minimization may be achieved by providing a sufficient number of biological particles (e.g., biological particles 114) at the partitioning junction 110, e.g., to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
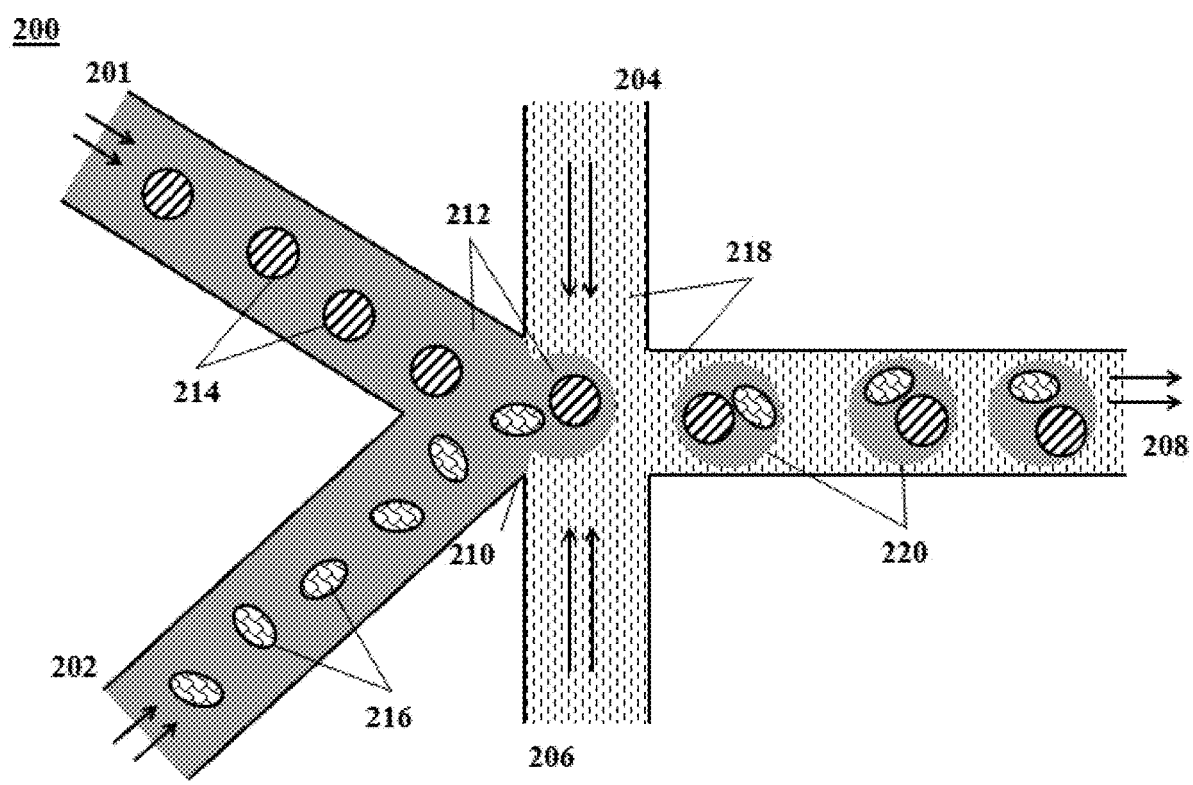
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, e.g., that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent e.g., tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, e.g., through passage of time or upon application of a particular stimulus, that degrades the microcapsule sufficiently to allow the biological particles (e.g., cell), or its other contents to be released from the microcapsule, e.g., into a partition (e.g., droplet). For example, in the case of the polyacrylamide polymer described above, degradation of the microcapsule may be accomplished through the introduction of an appropriate reducing agent, e.g., DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, e.g., nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals e.g., sodium hydroxide (NaOH) and/or endogenous chemicals e.g., inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets and other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, e.g., in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, e.g., barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, e.g., a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, e.g., droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, e.g., a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, e.g., size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars e.g., deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, e.g., the reaction of acrydite with other monomers and cross-linkers during a polymerization reaction. Acrydite moieties may be modified to form chemical bonds with a species to be attached, e.g., a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, e.g., for example, a P5 sequence for Illumina® sequencing. In some cases, the nucleic acid molecule or derivative thereof (e.g., oligonucleotide or polynucleotide generated from the nucleic acid molecule) can comprise another functional sequence, e.g., for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
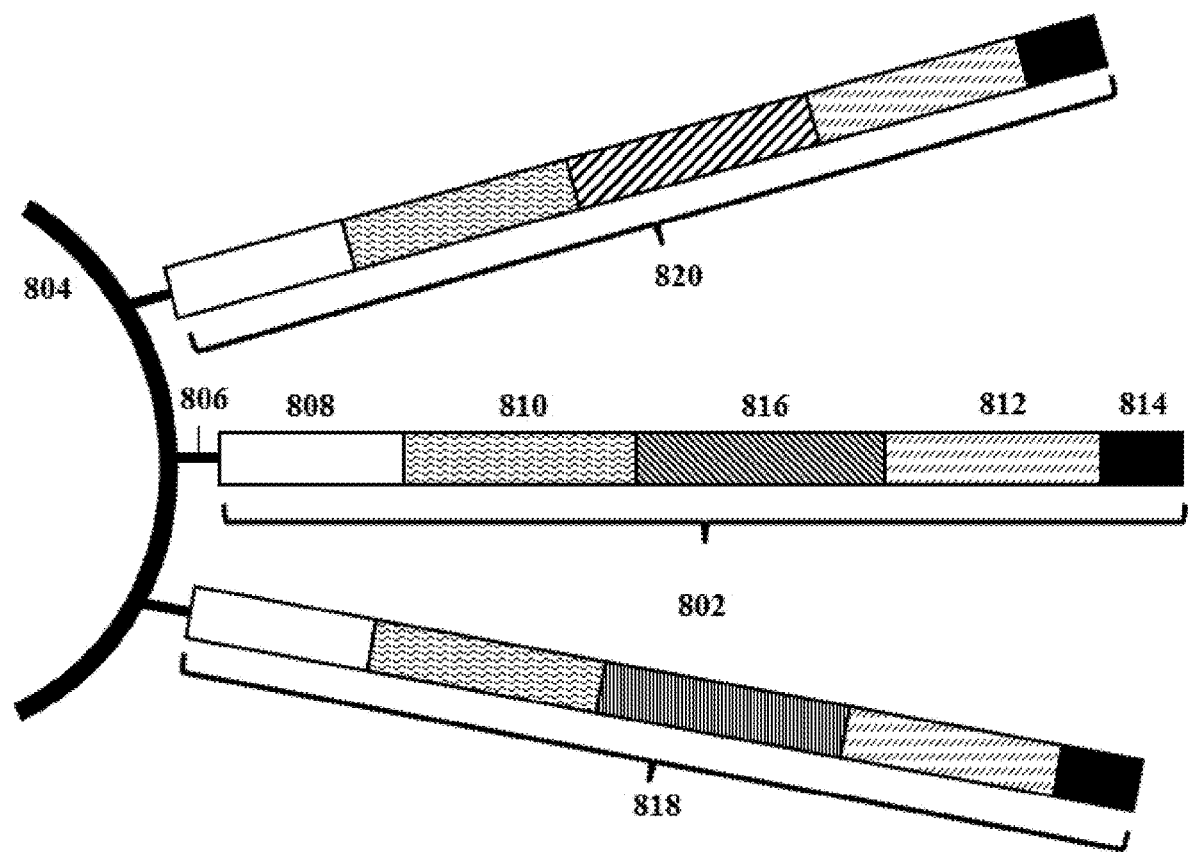
FIG. 8 illustrates an example of a barcode carrying bead.

FIG. 8 illustrates an example of a barcode carrying bead. A nucleic acid molecule 802, e.g., an oligonucleotide, can be coupled to a bead 804 by a releasable linkage 806, e.g., a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, e.g., an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, e.g., a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., e.g., a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NETS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent e.g., N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent: gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, e.g., fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, e.g., described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, e.g., barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, e.g., a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, e.g., a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, e.g., chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, e.g., restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions e.g., polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, e.g., disulfide groups, it will be desirable to avoid contacting such beads with reducing agents, e.g., DTT or other disulfide cleaving reagents. In such cases, treatment to the beads described herein will, in some cases be provided free of reducing agents, e.g., DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, e.g., BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, e.g., dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, e.g., an increase in pH, may trigger degradation of a bead. In other cases, exposure to an aqueous solution, e.g., water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, e.g., DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), e.g., through an additional channel or channels upstream of the channel junction. In accordance with other aspects, additionally or alternatively, biological particles may be partitioned along with other reagents, as will be described further below.

Figure 3:
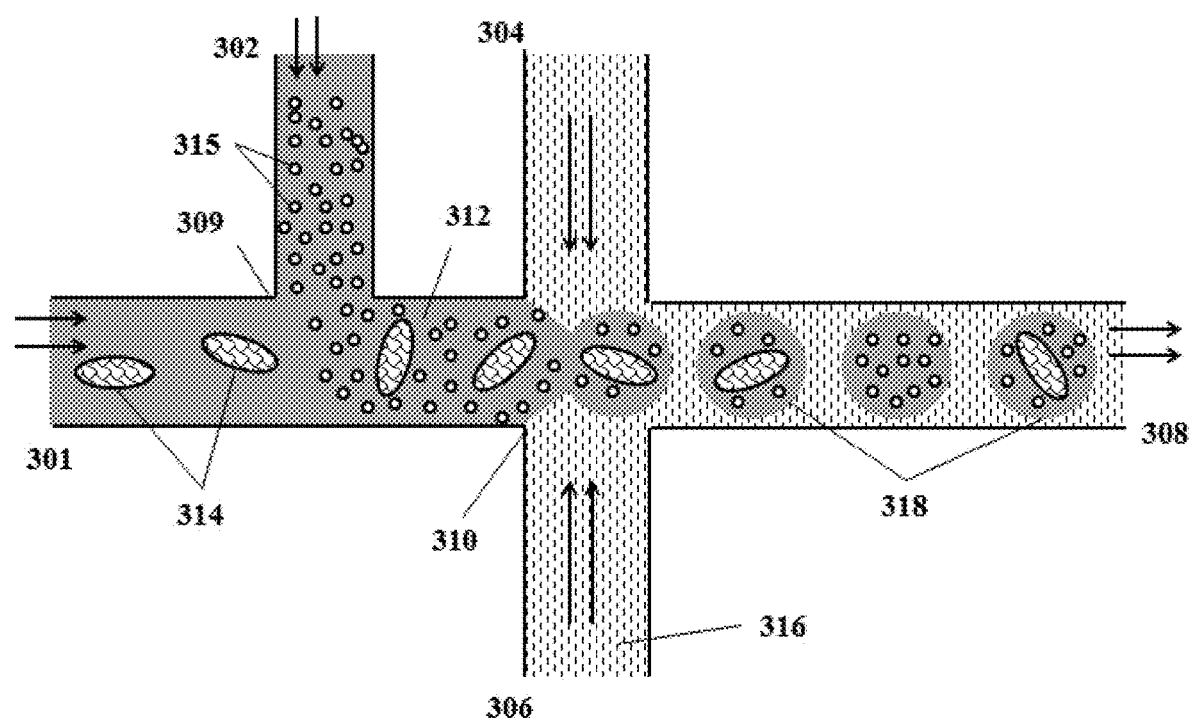
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, e.g., a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), e.g., via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, e.g., lysis enzymes that are used for lysis of different cell types, e.g., gram positive or negative bacteria, plants, yeast, mammalian, etc., e.g., lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particles's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants e.g., TritonX-100 and Tween 20. In some cases, lysis solutions may include ionic surfactants e.g., for example, sarcosyl and sodium dodecyl sulfate (SDS). Electroporation, thermal, acoustic or mechanical cellular disruption may also be used in certain cases, e.g., non-emulsion based partitioning e.g., encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, e.g., proteinase K, chelating agents, e.g., EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, e.g., endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, e.g., RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, e.g., described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, e.g., beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, e.g., DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
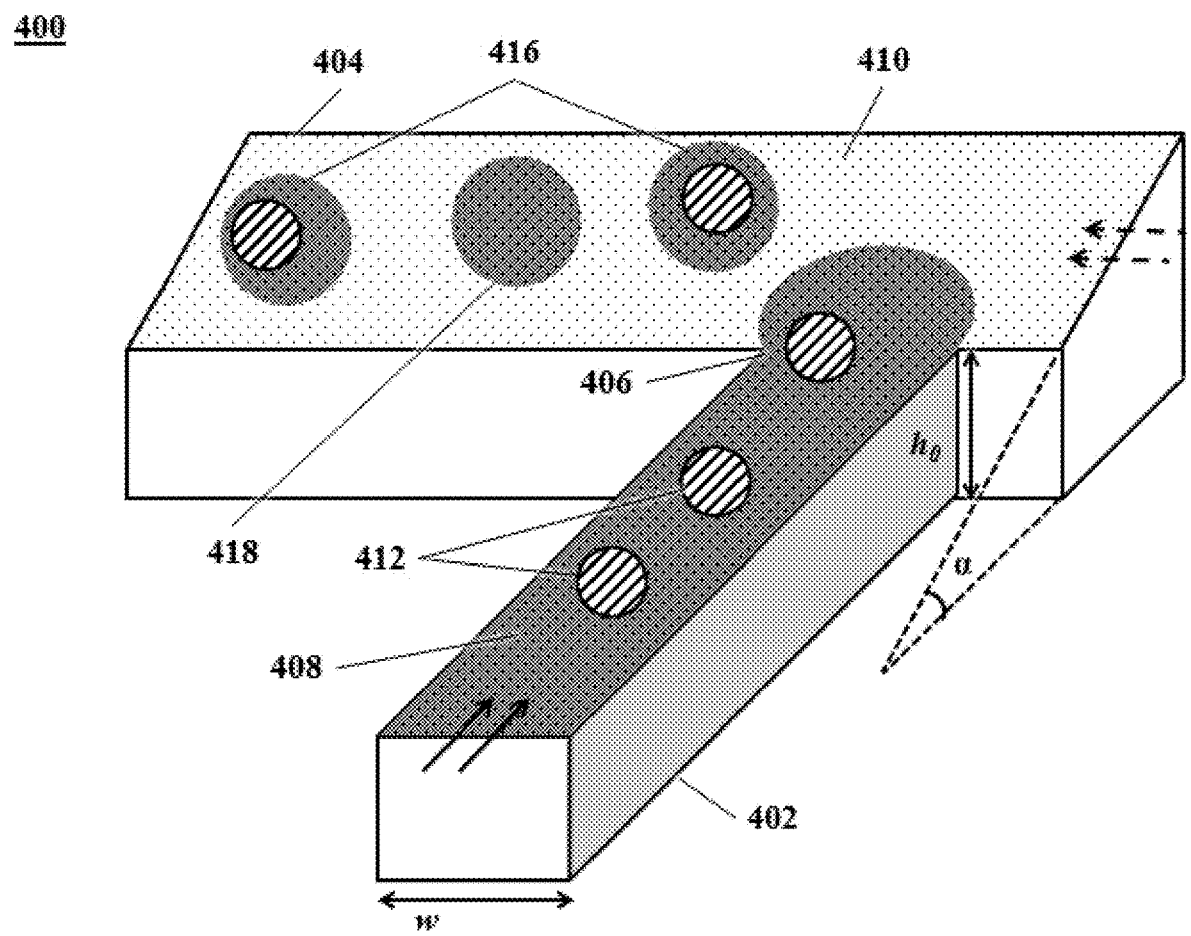
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors e.g., the hydrodynamic forces at the junction 406, flow rates of the two fluids 408, 410, fluid properties, and certain geometric parameters (e.g., w, $h_0$, a, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, e.g., a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, e.g., via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (e.g., in width or diameter). Alternatively, the cross-section of the channel segment 402 can be other shapes, e.g., a circular shape, trapezoidal shape, polygonal shape, or any other shapes. The top and bottom walls of the reservoir 404 at or near the junction 406 can be inclined at an expansion angle, $\alpha$. The expansion angle, $\alpha$, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, e.g., 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, e.g., flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, e.g., increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
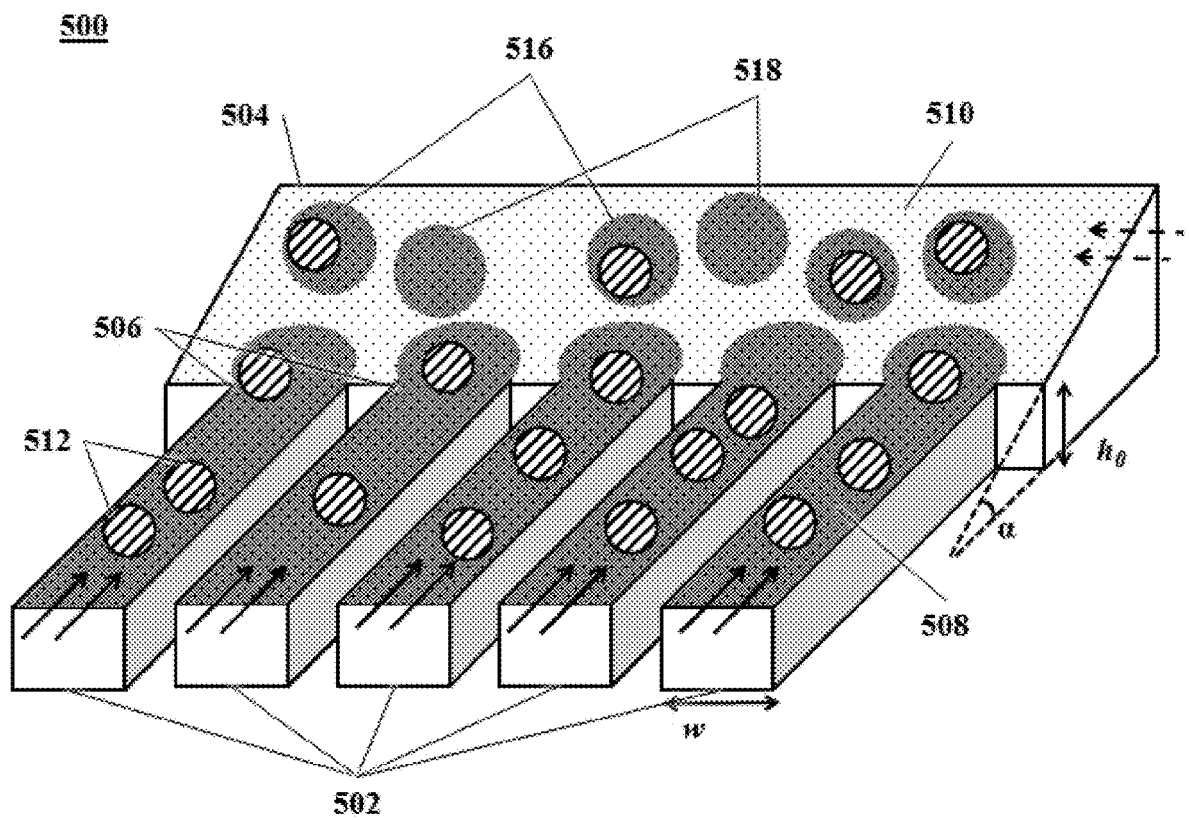
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, e.g., via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors e.g., the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
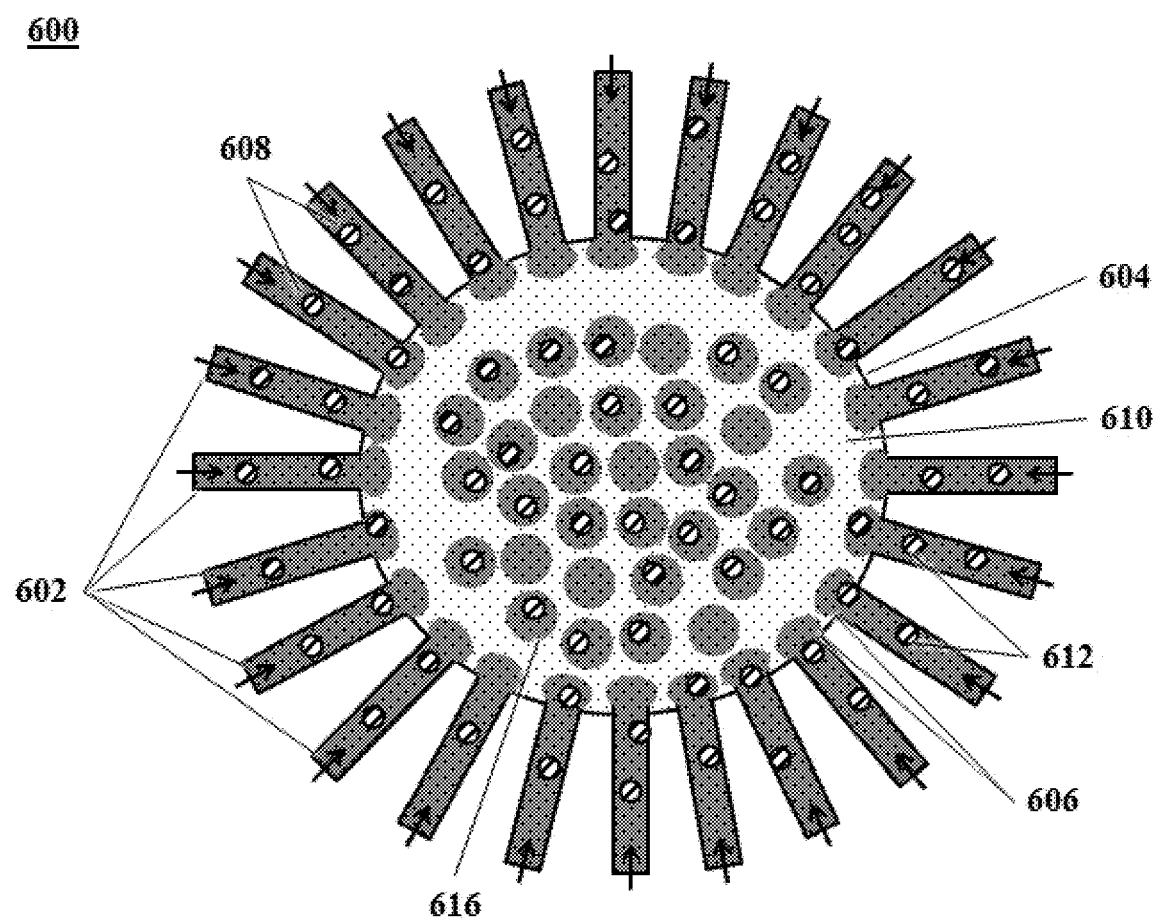
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, e.g., via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors e.g., the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors e.g., the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, e.g., a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, e.g., via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 µm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 µm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 µm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (µL)/minute (min) and about 40 µL/min. In some instances, the flow rate of the aqueous fluid 712 entering the junction 706 can be between about 0.01 microliters (µL)/minute (min) and about 100 µL/min. Alternatively, the flow rate of the aqueous fluid 712 entering the junction 706 can be less than about 0.01 µL/min. Alternatively, the flow rate of the aqueous fluid 712 entering the junction 706 can be greater than about 40 µL/min, e.g., 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, e.g., flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, e.g., at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, $\beta$), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Barcode Exchange

Disclosed herein, in some embodiments, are methods for nucleic acid processing, comprising: (a) in a plurality of partitions, using nucleic acid barcode molecules from a plurality of nucleic acid barcode molecules and a plurality of nucleic acid molecules (e.g., derived from a cell) to generate a plurality of barcoded nucleic acid molecules; (b) recovering the plurality of barcoded nucleic acid molecules from the plurality of partitions, to yield a mixture comprising the plurality of nucleic acid barcode molecules and a remainder of the plurality of nucleic acid barcode molecules; (c) subsequent to (b), subjecting the mixture to conditions sufficient to couple a blocking oligonucleotide to the remainder of the plurality of nucleic acid barcode molecules, wherein the blocking oligonucleotide comprises: (i) a complementary region comprising a sequence at least 75% complementary to a sequence in the remainder of the plurality of nucleic acid barcode molecules; and (ii) a 3' blocking group.

In some embodiments, the methods for nucleic acid processing disclosed herein comprise single-cell Assay for Transposase Accessible Chromatin with high-throughput sequencing (ATAC-seq). Exemplary methods for single cell ATAC-seq can be found, for example, in U.S. Pat. Pub. No. 20180340169, which is hereby incorporated by reference in its entirety.

Figure 10A:
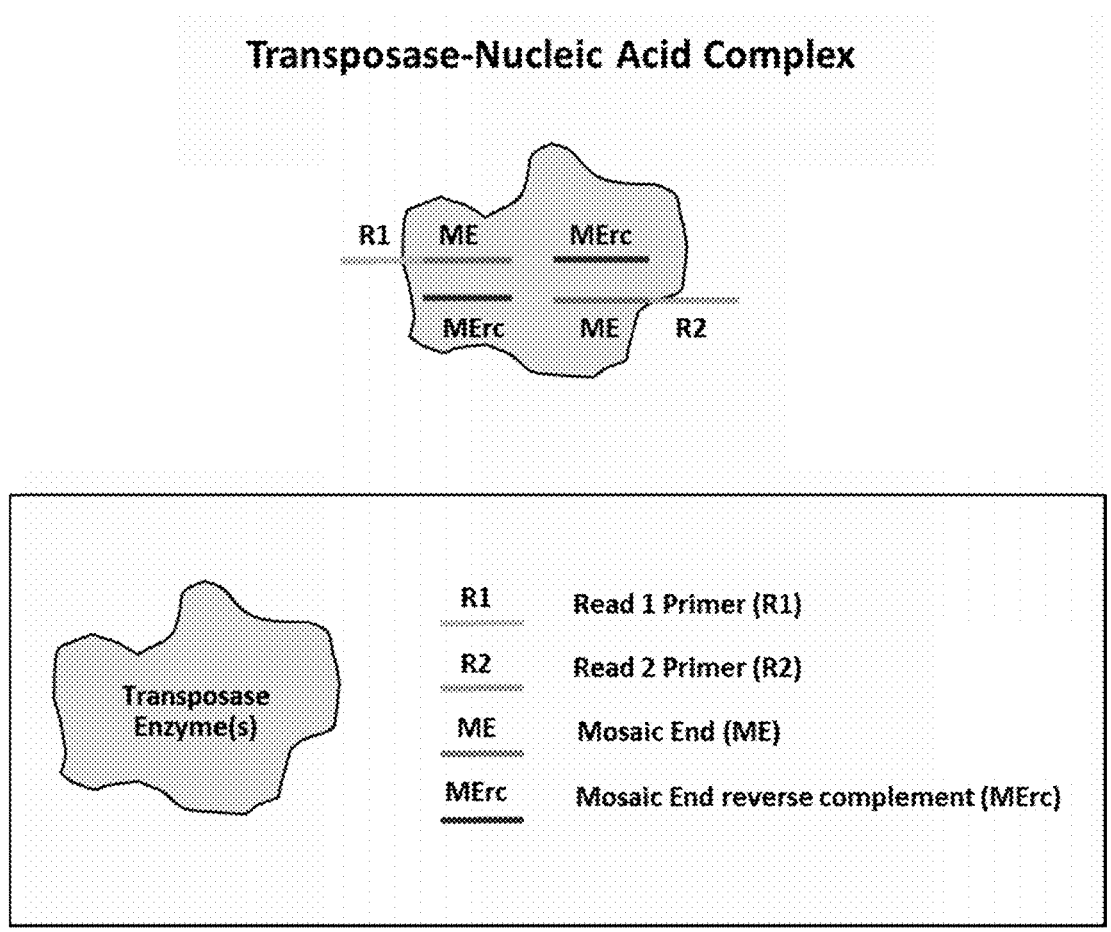
FIG. 10A illustrates an exemplary two-adapter transposase-nucleic acid complex for use in Tn5 mediated tagmentation reactions of chromatin.

In the ATAC-seq method, chromatin comprising genomic DNA from a cell or nucleus is tagged and fragmented (tagmented, also referred to as tagmentation) using a transposase nucleic acid complex comprising transposase molecules (e.g., a Tn5 transposase) loaded with transposon end sequence containing nucleic acid molecules. In some cases, the transposon end sequence containing nucleic acid molecules further comprise adapter sequences (e.g., sequencing primer sequences, for example an Illumina R1 or R2 sequencing primer sequence). See, e.g., FIG. 10A. The tagmented nucleic acid molecule (e.g., genomic DNA in chromatin) may also comprise transposon end sequences (e.g., 1105 in FIG. 11). In some embodiments, the adapter sequences are used as hybridization sites for amplification or ligation-based barcoding schemes to attach a barcode sequence to adapter-flanked template nucleic acid fragments (See e.g., U.S. Pat. Pub. No. 20180340169, which is hereby incorporated by reference in its entirety). In some instances, the barcode containing oligonucleotide molecules comprise additional functional sequences (e.g., an Illumina P5 or P7 sequence or complements thereof). Subsequent to tagmentation, adapter-flanked nucleic acid molecules can be subjected to a gap-filling reaction (e.g., process 1170 in FIG. 11) to facilitate subsequent processing steps (e.g., linear amplification-based barcoding schemes 1180 in FIG. 11 and as described further herein). A nucleic acid reaction, e.g., a linear amplification may be repeated one or more times, as exemplified in process 1190 of FIG. 11. In some instances, the gap-filling reaction 1170 occurs in the partition. The gap-filling reaction 1170 may also occur outside a partition (e.g., in bulk).

Figure 10B:
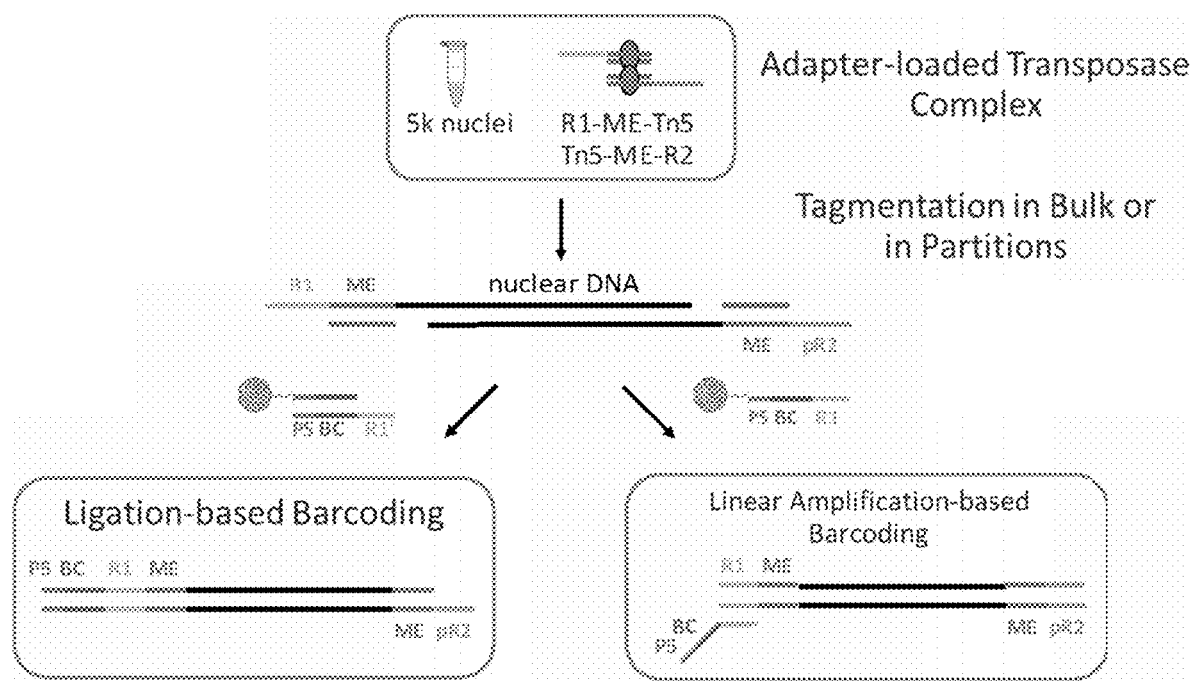
FIG. 10B illustrates partition-based barcoding of tagmented nuclear DNA using either a ligation-based or linear-amplification-based barcode conjugation method.

In some embodiments, linear-amplification-based barcode conjugation is used to barcode tagmented, adapter-flanked template DNA (see, e.g., FIG. 10B). In some embodiments, linear-amplification-based barcode conjugation schemes comprise in-partition barcode attachment with additional processing steps performed in bulk (see, e.g., FIG. 11). In some instances, linear amplification occurs in a partition (e.g., droplet emulsion). In some examples, linear amplification in the partition occurs wherein a nucleic acid barcode molecule is coupled to a solid support. In some instances, the solid support is a bead. In some embodiments, the solid support is a gel bead. In some instances, the nucleic acid barcode molecules are releasably attached to the solid support. In some embodiments, the solid support is a glass or quartz surface. In some embodiments, the solid support may form a partition or well. The nucleic acid barcode molecules may comprise an adapter sequence (e.g., an Illumina P5 sequence, e.g., 1110), a barcode sequence (e.g., 1120), and a primer sequence (e.g., a sequencing primer sequence 1130 and 1130b, for example an Illumina R1 or R2 sequencing primer sequence or a sequence complementary to an R1 or R2 sequence). Additionally or alternatively, the barcode molecule may comprise any combination or variations of functional sequences, e.g., a spacer sequence, a unique molecular identifier, a binding sequence, a restriction site, etc. In some embodiments, barcoded, adapter-flanked template nucleic acid fragments are generated by annealing a nucleic acid barcode molecule to a complementary region (e.g., the R1 adapter sequence) on the adapter-flanked template nucleic acid fragment, which is extended in a linear amplification (e.g., 1180 and 1190) reaction using a polymerase, as illustrated in FIG. 11.

Figure 17:
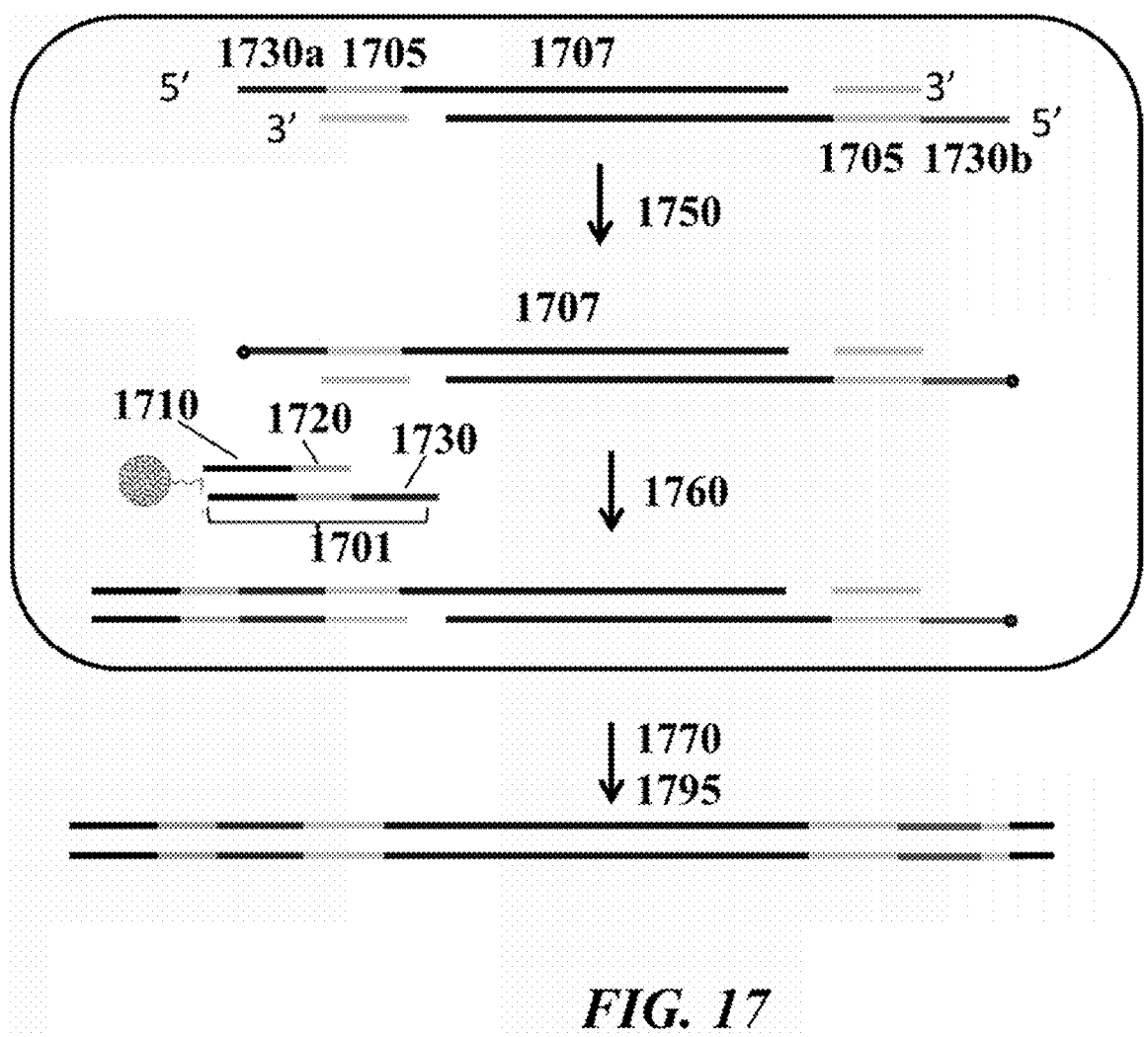
FIG. 17 shows a schematic of a method of processing nucleic acid molecules in partitions.

In some embodiments, ligation-based barcode conjugation is used to barcode the tagmented nucleic acid molecule, e.g., tagmented, adapter-flanked template DNA (see, e.g., FIG. 10B, FIG. 17 and U.S. Pat. Pub. No. 20180340169, which is hereby incorporated by reference in its entirety). The nucleic acid barcode molecule (e.g., 1701), which may be partially double-stranded, may comprise an adapter sequence (e.g., a primer annealing sequence or a functional sequence, e.g. an Illumina P5 sequence as shown in 1110, 1210, 1310, 1710 and 1810), a barcode sequence (e.g., 1120, 1320, 1720, 1820), and a primer sequence (e.g., a sequencing primer sequence, for example an Illumina R1 or R2 sequencing primer sequence or a sequence complementary to an R1 or R2 sequence, e.g., 1130, 1230, 1330 and 1730). The tagmented nucleic acid molecule may also comprise transposon end sequences (e.g., 1705), or a complement thereof. Additionally or alternatively, the nucleic acid barcode molecule (e.g., 1701) may comprise any combination or variations of functional sequences, e.g., a spacer sequence, a unique molecular identifier, a binding sequence, a restriction site, etc., or complements thereof. The nucleic acid barcode molecule 1701 may associate with the tagmented, adapter-flanked template DNA 1707 (e.g., by hybridization). In some cases, one or more sequences (e.g., 1730) on the nucleic acid barcode molecule 1701 may be an overhang sequence (e.g. 5' overhang) and may be complementary and capable of annealing to one or more sequences on the tagmented, adapter-flanked template DNA. In some cases, the tagmented adapter-flanked template DNA may be treated, e.g., in process 1750, with an enzyme, e.g., T4 polynucleotide kinase, to phosphorylate the 5' ends. The nucleic acid barcode molecule 1701 may then be ligated to the tagmented, adapter-flanked template DNA using an enzyme, e.g., a ligase (e.g., T4 DNA ligase) to generate a barcoded nucleic acid molecule, e.g., a barcoded, adapter-flanked template nucleic acid fragment. In some examples, the nucleic acid barcode molecule is coupled to a solid support. In some instances, the solid support is a bead. In some embodiments, the solid support is a gel bead as described elsewhere herein. In some instances, the nucleic acid barcode molecules are releasably attached to the solid support.

Figure 11:
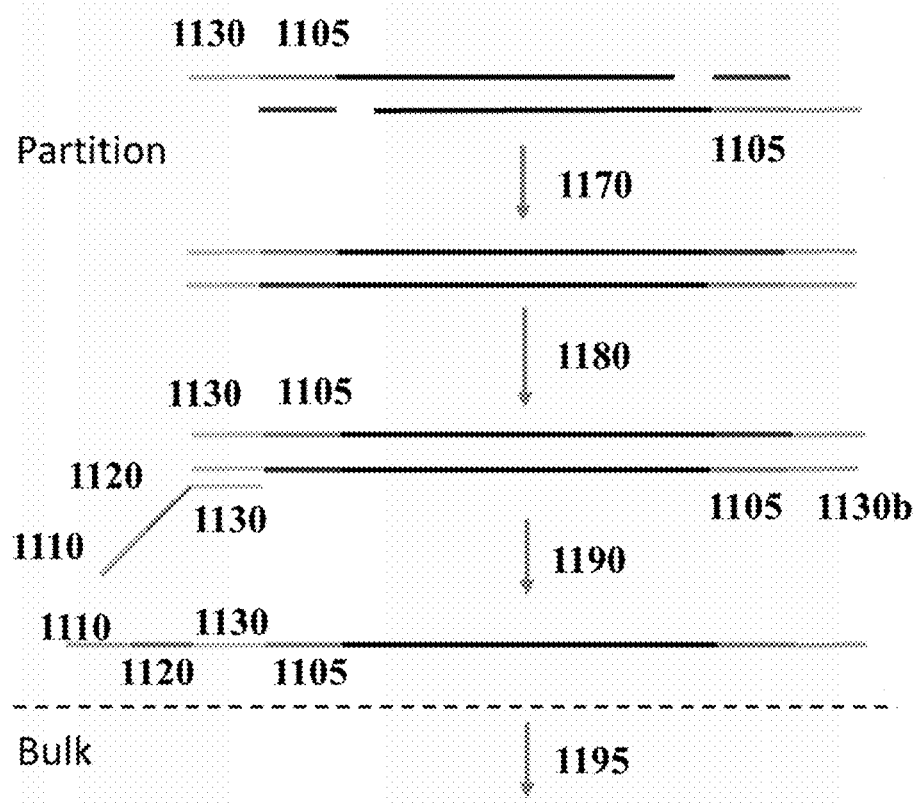
FIG. 11 shows an exemplary linear amplification-based barcoding scheme showing in-partition barcode and adapter sequence attachment with additional processing steps performed in bulk.

In some embodiments, following the barcoding reaction, the barcoded, adapter-flanked template nucleic acid fragments are removed from the partitions (e.g., the droplet emulsion is broken or disrupted), in some instances purified, and combined together in bulk for sample indexing polymerase chain reaction (SI-PCR, e.g., 1195, 1795), e.g., as shown in FIGS. 11, 17. In some instances, the barcoded, adapter-flanked template nucleic acid fragments are subjected to conditions sufficient for gap filling (e.g., process 1770). Gap-filling may occur, for example, using an enzyme, e.g., a polymerase and/or ligase. In some cases, SI-PCR (e.g., 1195, 1795) comprises one or more PCR reactions that serve to add additional sequences (e.g., a P7 or sample index sequence (e.g., i7)) to the barcoded, adapter-flanked nucleic acid fragments to prepare these fragments for high throughput sequencing (e.g., Illumina sequencing). In some circumstances, excess nucleic acid barcode molecules that are not incorporated during linear amplification can be carried over from the partitions into the bulk SI-PCR reaction. In these instances, during bulk SI-PCR, the excess barcode molecules can prime template nucleic acid fragments resulting in PCR products that contain a different barcode sequence than the parent template molecule (a process known as "barcode exchange" or a "barcode exchange reaction").

Figure 12A:
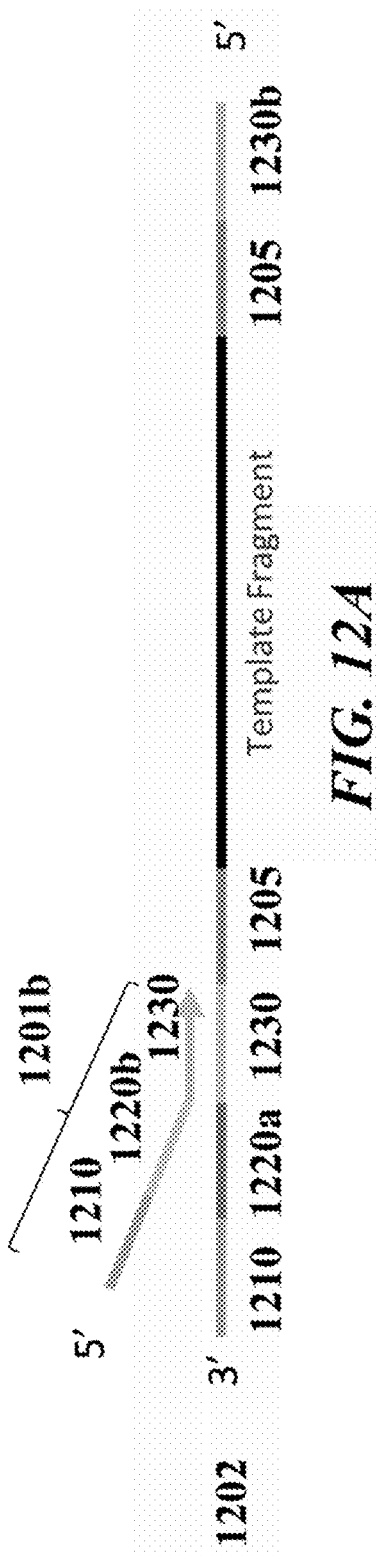
FIG. 12A shows a schematic of a representative barcode exchange reaction.

A representative example of a barcode exchange reaction is shown in FIG. 12A. After barcoded, adapter-flanked template nucleic acid molecules 1202 are removed from partitions and combined in a bulk SI-PCR reaction, the bulk mixture comprises barcoded fragments, each with a specific barcode sequence that is indicative of and associates barcoded fragments as arising from a single cell. FIG. 12A shows a representative barcoded, adapter-flanked template nucleic acid molecule 1202 comprising barcode sequence 1220a. The adapter-flanked template nucleic acid molecule 1202 may also comprise an adapter sequence 1210 (e.g., P5 sequence), a sequencing primer sequence 1230 and 1230b (e.g., R1 or R2 sequence) and/or a transposon end sequence 1205, or any complements thereof. Carry-over of excess nucleic acid barcode molecules 1201b, which may comprise a different barcode sequence 1220b, from a partition (e.g., the linear amplification primers shown in FIG. 11) can result in the undesired priming and amplification during SI-PCR resulting in barcode exchange. For example, FIG. 12A shows an exemplary carried-over nucleic acid barcode molecule comprising barcode sequence 1220b. During SI-PCR, this barcode molecule 1201b comprising barcode sequence 1220b can hybridize and amplify the 1220a-containing fragment to produce a 1220b-containing template nucleic acid molecule, thereby exchanging the 1220a barcode sequence for the 1220b barcode sequence. Because the 1220a barcode is indicative of a particular single cell, the exchanged barcode interferes with efficient single cell analysis by contributing to wasted and inaccurate data.

Figure 12B:
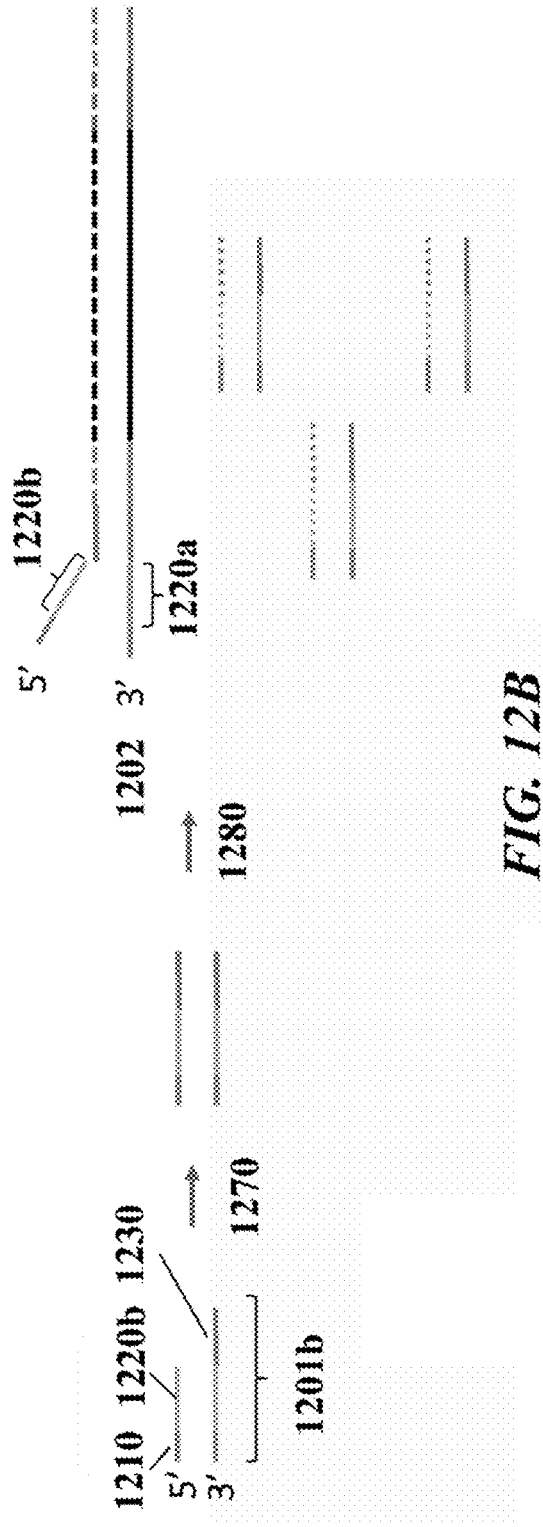
FIG. 12B shows a schematic of a mechanism for barcode exchange after ligation based barcode conjugation.

An exemplary mechanism for a barcode exchange reaction is shown in FIG. 12B. After the barcoded, adapter-flanked template nucleic acid molecules are removed from partitions and combined in a bulk SI-PCR reaction, any remaining unbound nucleic acid barcode molecules (e.g., 1201b) may be amplified. In some cases, the nucleic acid barcode molecules 1201b may be partially double-stranded and may be subjected to a gap-fill reaction 1270 (e.g., the 3' end of the top strand of the nucleic acid barcode molecule 1201b is extended using the R1 sequence in the bottom strand as a template using an enzyme [e.g., polymerase]) prior to amplification 1280 (e.g., linear amplification or SI-PCR). The nucleic acid barcode molecules 1201b may also comprise an adapter sequence 1210 (e.g., P5 sequence), which may be substantially similar to e.g., 1110, 1310, 1410, and 1810 and a sequencing primer sequence 1230, which may be substantially similar to, e.g., 1130, 1330, 1430, and 1830 or complements thereof. During an amplification reaction 1280 (e.g., linear amplification or SI-PCR), part of the nucleic acid barcode molecule 1201b (e.g., one of the strands) may participate in a barcode exchange reaction. For example, as shown in FIG. 12A, a barcode molecule 1201b comprising barcode sequence 1220b may hybridize (e.g., via sequence complementarity of adapter sequence 1230) to the adapter-flanked template nucleic acid molecule 1202 comprising barcode sequence 1220a. An amplification reaction may then result in exchange of the 1220a barcode sequence for the 1220b barcode sequence. In addition, a part of the nucleic acid barcode molecule 1201b (e.g., one of the strands) may be amplified, generating extra double-stranded nucleic acid barcode molecules. During nucleic acid amplification, these extra nucleic acid barcode molecules may also participate in barcode exchange reactions, as described herein, and contribute to wasted and inaccurate data.

In some embodiments, barcode exchange can be prevented or reduced by removing excess barcoded primer through size-dependent purification on diethylaminoethyl cellulose (DEAE) membranes. In some embodiments, barcode exchange can be prevented or reduced by removing excess barcoded primer using Solid Phase Reversible Immobilization (SPRI). In some instances, however, such purification steps performed before library amplification can cause the loss of unique molecules in a sequencing library, thus, reducing library complexity.

In some embodiments, the present disclosure provides methods to minimize barcode exchange. In some embodiments, the present disclosure provides methods to minimize barcode exchange using oligonucleotides containing a 3'-terminated chemical block that cannot be extended by a polymerase.

Hairpin Cap Molecule to Minimize Barcode Exchange

Disclosed herein, in some embodiments, are methods for nucleic acid processing, comprising: (a) in a plurality of partitions, using nucleic acid barcode molecules from a plurality of nucleic acid barcode molecules and a plurality of nucleic acid molecules to generate a plurality of barcoded nucleic acid molecules; (b) recovering the plurality of barcoded nucleic acid molecules from the plurality of partitions, to yield a mixture comprising the plurality of nucleic acid barcode molecules and a remainder of the plurality of nucleic acid barcode molecules; (c) subsequent to (b), subjecting the mixture to conditions sufficient to couple a blocking oligonucleotide to the remainder of the plurality of nucleic acid barcode molecules, wherein the blocking oligonucleotide comprises: (i) a complementary region comprising a sequence at least 75% complementary to a sequence in the remainder of the plurality of nucleic acid barcode molecules; and (ii) a 3' blocking group.

In some instances, the plurality of partitions is a plurality of droplets. In some instances, the plurality of partitions is a plurality of wells.

In some embodiments, the blocking oligonucleotides of the present disclosure comprise, from 5' to 3', a first stem sequence, a loop sequence, a second stem sequence at least 75% complementary to the first stem sequence, and a sequence at least 75% complementary to a sequence in a remainder of nucleic acid barcode molecules. In some embodiments, the second stem sequence is 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to the first stem sequence. In some embodiments, the second stem sequence comprises a region that is 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to the first stem sequence. For example, in some instances, the first stem sequence comprises (1) one or more regions at least 75% complementary to the second stem sequence, and (2) one or more internal loops that are not complementary to the second stem sequence. In some embodiments, the second stem sequence comprises (1) one or more regions at least 75% complementary to the first stem sequence, and (2) one or more internal loops that are not complementary to the first stem sequence. In some embodiments, the blocking oligonucleotide comprises a sequence that is 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to a sequence in the remainder of the plurality of nucleic acid barcode molecules.

Figure 13A:
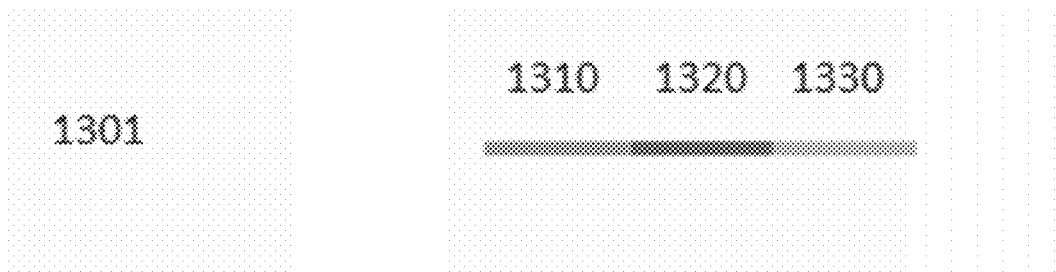
FIGS. 13A-13C illustrate a design of a representative hairpin cap to prevent barcode exchange.
Figure 13B:
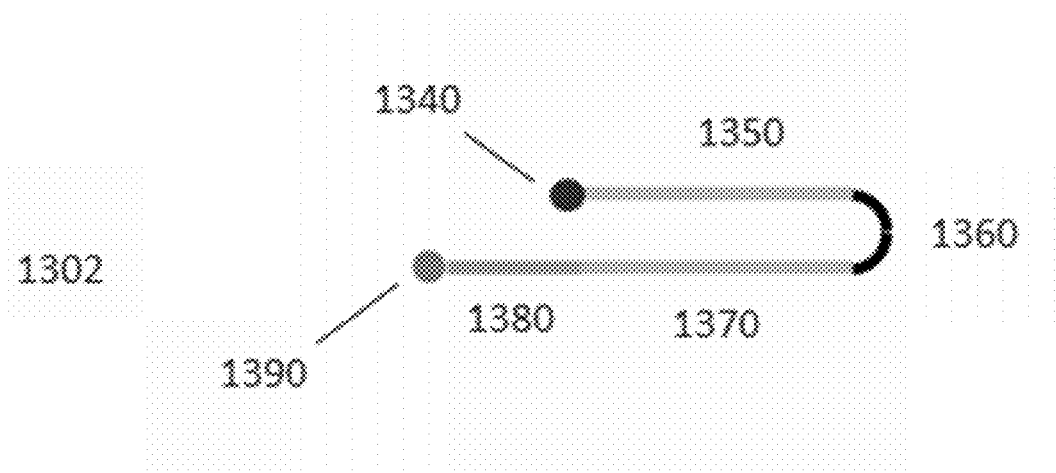
Figure 13C:
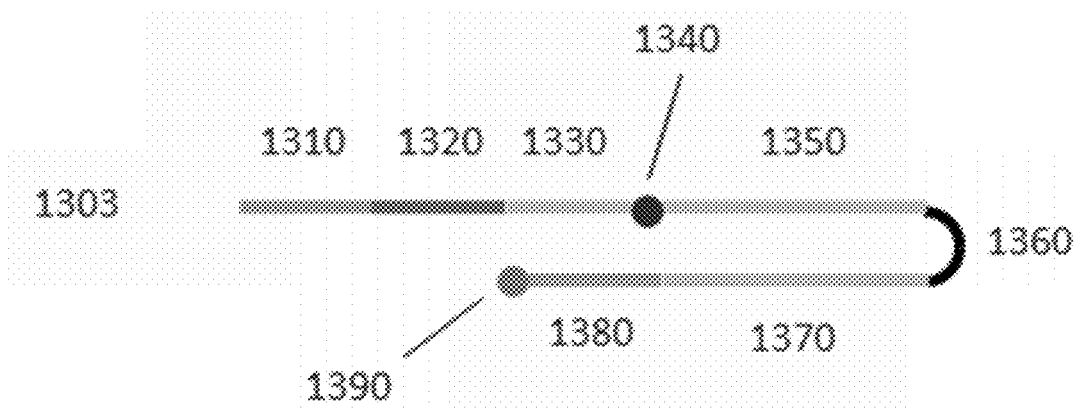

FIG. 13A shows a representative remainder (i.e., carried over from a partition) nucleic acid barcode molecule 1301 wherein 1310 represents an adapter sequence (e.g., a P5 sequence), 1320 represents a barcode sequence, and 1330 represents a primer sequence (e.g., a R1 sequencing primer sequence). FIG. 13B shows a representative blocking oligonucleotide 1302 wherein 1340 represents a 5' phosphate group, 1350 represents a first stem sequence, 1360 represents a loop sequence, 1370 represents a second stem sequence complementary to the first stem sequence, 1380 represents a sequence complementary to a sequence (1330) in a remainder of nucleic acid barcode molecules, and 1390 represents a 3' blocking group that prevents extension by a polymerase and/or ligation. FIG. 13C shows a representative capped barcode molecule 1303 wherein the blocking oligonucleotide 1302 has been ligated to a remainder nucleic acid barcode molecule 1301. To aid in the ligation process, blocking oligonucleotide sequence 1380 hybridizes to complementary sequence 1330 while 3' blocking group 1390 prevents the capped barcode molecule 1303 from participating in a barcode exchange reaction.

The sequence and length of the first and/or second stem sequence of the blocking oligonucleotide may be altered, wherein the sequence maintains its complementary region and forms a hairpin structure with itself. In some embodiments, the blocking oligonucleotide is referred to as a hairpin cap due to its hairpin structure and thus, in used herein, blocking oligonucleotide and hairpin cap are used interchangeably. In some instances, the blocking oligonucleotide does not form a hairpin structure. In some instances, the blocking oligonucleotide dimerizes with another oligonucleotide, wherein the dimer efficiently blocks the carried over barcode molecule from being used during SI-PCR for barcode exchange.

In some embodiments, the sequence of the loop of the blocking oligonucleotide may be altered. In some instances, the size of the loop of the blocking oligonucleotide may be increased. In some instances, the size of the loop of the blocking oligonucleotide may be decreased. In some embodiments, an affinity handle is attached to the blocking oligonucleotide (e.g., in the loop sequence), wherein affinity handle is used to purify the blocking oligonucleotide and/or ligated hairpin-capped barcode molecule. In some cases, the affinity handle is a biotin group, but can comprise any suitable affinity handle to facilitate purification of the blocking oligonucleotide or a derivative thereof.

In some embodiments, the 3' blocking group is configured to prevent ligation of the remainder to a nucleic acid molecule. In some instances, the 3' blocking group is configured to prevent extension of the primer sequence when hybridized to a target nucleic acid molecule. In some embodiments, the 3' blocking group is at a 3' terminus of the blocking oligonucleotide. In some embodiments, the 3' blocking group is a 2'-3'-dideoxycytosine (ddC). In some embodiments, the 3' blocking group is a 2'-5' linked nucleoside. In some embodiments, the 3' blocking group is a 3' C3 spacer. In some embodiments, the 3' blocking group is an amino-modified C6. In some embodiments, the 3' blocking group is an inverted deoxythymidine (dT). In some embodiments, the 3' blocking group is a 3' amino modified nucleotide. In some embodiments, the 3' blocking group is 3' phosphate group. In some embodiments, the 3' blocking group is a 2'-5' linked nucleoside, wherein the 2'-5' linked nucleoside is a 3'-deoxythymidine (3'-dT). In some instances, the 2'-5' linked nucleoside is a 3'-deoxycytidine (3'-dC). In some instances, the 2'-5' linked nucleoside is a 3'-deoxyadenosine (3'-dA). In some instances, the 2'-5' linked nucleoside is a 3'-deoxyguanosine (3'-dG).

Disclosed herein, in some embodiments, are compositions comprising, from 5' to 3': (a) a first region comprising a barcode sequence and a primer sequence; and (b) a second region comprising (i) a sequence complementary to the primer sequence; and (ii) a 3' blocking group. A representative composition is shown in FIG. 13B. In some embodiments, the sequence complementary to the primer sequence is 75% 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% complementary to the primer sequence.

In some embodiments, the 3' blocking group of the compositions disclosed herein is at a 3' terminus of the blocking oligonucleotide. In some embodiments, the 3' blocking group of the compositions disclosed herein is a 2'-3'-dideoxycytosine (ddC). In some embodiments, the 3' blocking group of the compositions disclosed herein is a 2'-5' linked nucleoside. In some embodiments, the 3' blocking group of the compositions disclosed herein is a 3' C3 spacer. In some embodiments, the 3' blocking group of the compositions disclosed herein is an amino-modified C6. In some embodiments, the 3' blocking group of the compositions disclosed herein is an inverted deoxythymidine (dT). In some embodiments, the 3' blocking group of the compositions disclosed herein is a 3' amino modified nucleotide. In some embodiments, the 3' blocking group of the compositions disclosed herein is a 3' phosphate group. In some embodiments, the 3' blocking group of the compositions disclosed herein is a 2'-5' linked nucleoside, wherein the 2'-5' linked nucleoside is a 3'-deoxythymidine (3'-dT). In some instances, the 2'-5' linked nucleoside of the compositions disclosed herein is a 3'-deoxycytidine (3'-dC). In some instances, the 2'-5' linked nucleoside of the compositions disclosed herein is a 3'-deoxyadenosine (3'-dA). In some instances, the 2'-5' linked nucleoside of the compositions disclosed herein is a 3'-deoxyguanosine (3'-dG).

In some embodiments, the second region of the composition of the present disclosure comprises, from 5' to 3': a first stem sequence, a loop sequence, a second stem sequence at least 75% complementary to the first stem sequence, a sequence complementary to the primer sequence, and the 3' blocking group (FIG. 13B). In some embodiments, the second stem sequence of the compositions disclosed herein is 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% complementary to the first stem sequence.

The blocking oligonucleotides disclosed herein are also useful in preventing unwanted interactions in a variety of nucleic acid based reactions. For example, the blocking oligonucleotides disclosed herein may be utilized to block, inhibit, or otherwise alter the rate of a PCR reaction (e.g., in situations where (1) a purification step cannot be performed or is unideal or (2) to minimize a PCR reaction primed from one or more specific primers or primer sets in a sample).

Minimizing Barcode Exchange Using RNase

Figure 14A:
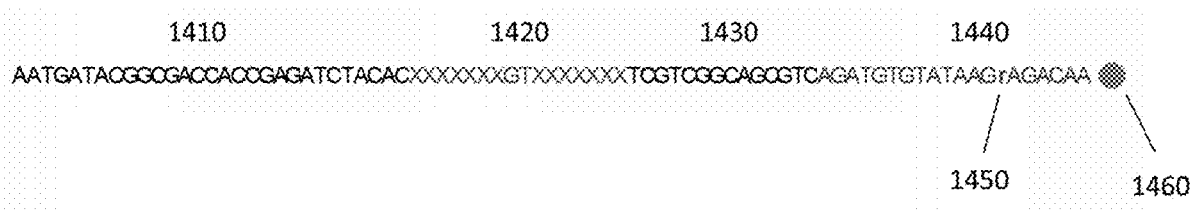
FIGS. 14A-C illustrates an exemplary ribonucleotide-containing barcode molecule containing a 3' blocking group.
Figure 14B:
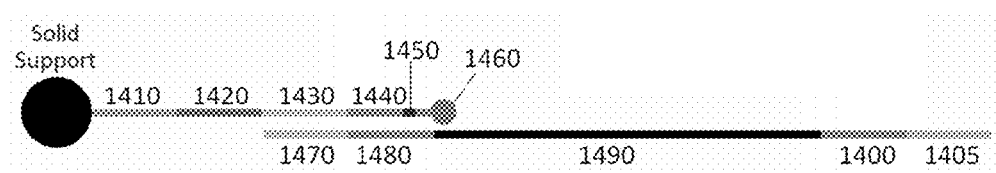
Figure 14C:
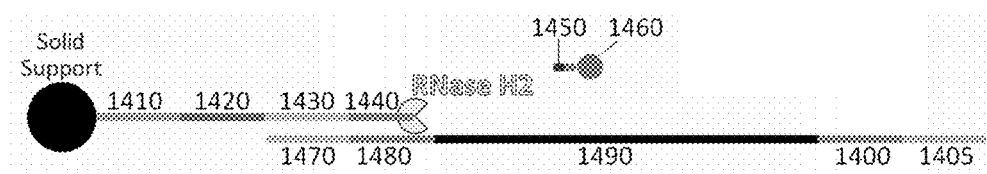

Disclosed herein, in some embodiments, are methods for nucleic acid processing, comprising: (a) providing a reaction mixture comprising: (i) a template nucleic acid molecule; (ii) an RNase enzyme; and (iii) a plurality of nucleic acid barcode molecules, wherein each nucleic acid barcode molecule of the plurality of nucleic acid barcode molecules comprises: (A) a common barcode sequence; (B) a sequence capable of hybridizing to a target nucleic acid; (C) at least one ribonucleotide; and (D) a 3' blocking group; (b) subjecting the reaction mixture to conditions sufficient for the template nucleic acid molecule to hybridize to a nucleic acid barcode molecule of the plurality of nucleic acid barcode molecules; (c) subjecting the reaction mixture to conditions sufficient for the RNase enzyme to degrade the ribonucleotide, thereby releasing the 3' blocking group; and (d) using the template nucleic acid molecule and the nucleic acid barcode molecule to generate a barcoded template nucleic acid molecule (FIG. 14A-C).

In some embodiments, the 3' blocking group is configured to prevent ligation of the remainder to a nucleic acid molecule. In some instances, the 3' blocking group is configured to prevent extension of the primer sequence when hybridized to a target nucleic acid molecule. In some instances, the barcode sequence is 5' to at least one ribonucleotide and the 3' blocking group and is not released from the nucleic acid barcode molecule.

In some embodiments, the 3' blocking group is at a 3' terminus of the plurality of nucleic acid barcode molecules. In some instances, the 3' blocking group is a 2'-3'-dideoxycytosine (ddC). In some instances, the 3' blocking group is a 2'-5' linked nucleoside. In some instances, the 3' blocking group is a 3' C3 spacer. In some instances, the 3' blocking group is an amino-modified C6, an inverted deoxythymidine (dT). In some instances, the 3' blocking group is a 3' amino modified nucleotide. In some instances, the 3' blocking group is a 3' phosphate group. In some instances, the 3' blocking group is a 2'-5' linked nucleoside, wherein the 2'-5' linked nucleoside is a 3'-deoxythymidine (3'-dT). In some embodiments, the 2'-5' linked nucleoside is a 3'-deoxycytidine (3'-dC). In some embodiments, the 2'-5' linked nucleoside is a 3'-deoxyadenosine (3'-dA). In some embodiments, the 2'-5' linked nucleoside is a 3'-deoxyguanosine (3'-dG). In some embodiments, the 3' blocking group cannot be extended by a polymerase.

In some embodiments, the method of the present disclosure further comprises co-partitioning the reaction mixture into a partition. In some instances, the partition is a well. In some instances, the partition is an aqueous droplet in an emulsion.

In some embodiments, the plurality of nucleic acid barcode molecules is attached to a solid support. In some instances, the solid support is a bead. In some instances, the plurality of nucleic acid barcode molecules is releasably attached to the bead. In some instances, the bead is a gel bead. In some examples, the bead is a gel bead. In some embodiments, the gel bead is a degradable gel bead. In some instances, the degradable gel bead is degradable by a chemical stimulus. In some embodiments, the chemical stimulus is a reducing agent. In some embodiments, the reaction mixture comprises the reducing agent.

In some embodiment, the plurality of nucleic acid barcode molecules attached to the solid support (e.g., bead or gel bead) are modified to contain a ribonucleotide. In some instances, the ribonucleotide is approximately 4 to 8 nucleotides upstream from the 3' blocking group. In some embodiments, the ribonucleotide is approximately 4, 5, 6, 7, 8, or more nucleotides upstream from the 3' blocking group. Exemplary ribonucleotide-containing barcode molecules containing a 3' blocking group are shown in FIGS. 14A-C. Feature 1410 represents an adapter sequence, wherein in some instances, the adapter sequence is an Illumina P5 sequence. Feature 1420 represents a barcode sequence. Feature 1430 represents a primer sequence wherein, in some instances, the primer sequence is a sequencing primer sequence, e.g., an Illumina R1 sequencing primer sequence. Feature 1440 represents a transposon-end sequence wherein, in some instances, the transposon-end sequence is a 14 bp mosaic element. Feature 1450 represents a ribonucleotide. Feature 1460 represents a 3' blocking group, wherein, in some instances, the 3' blocking group is a C3 spacer. Features 1430 and 1440 are configured to be complementary to features 1470 and 1480 respectively in an adapter-flanked template nucleic acid molecule, with feature 1490 representing a template nucleic acid sequence and features 1400 and 1405 representing a transposon-end sequence and an adapter sequence (e.g., an Illumina R2 sequence), respectively.

In some embodiments, in the methods disclosed herein, the RNase enzyme is not capable of cleaving a single-stranded ribonucleotide-containing barcode molecule. In some embodiments, once the template nucleic acid molecule hybridizes to the nucleic acid barcode molecule creating an at least partially double-stranded region comprising the ribonucleotide, the RNase enzyme cleaves the ribonucleotide, thereby releasing the 3' blocking group. In some embodiments the RNase enzyme is an RNase H2 enzyme. In some embodiments, the RNase H2 enzyme is thermostable. In some embodiments, the RNase H2 enzyme does not cleave single stranded RNA. In some embodiments, the RNase H2 enzyme cleaves RNA in RNA:DNA duplexes. In some embodiments, the thermostable RNase H2 enzyme releases the 3' blocking group. In some examples, the thermostable RNase H2 enzyme releases the 3' blocking group as illustrated in FIG. 14C.

In some embodiments, the methods for nucleic acid processing disclosed herein comprise adding an adapter sequence to the template nucleic acid molecule prior to hybridization and barcoding with the nucleic acid barcode molecules described herein. In some instances, the adapter sequence is capable of hybridizing to a sequence on a nucleic acid barcode molecule (FIG. 14B). In some embodiments, the adapter sequence is added to the template nucleic acid molecule by a transposase (e.g., by a tagmentation reaction). In some embodiments, the adapter sequence comprises a sequencing primer sequence. In some instances, the primer sequence is annealed to a complementary sequence in a nucleic acid barcode molecule comprising a ribonucleotide and a 3' blocking group, wherein the 3' blocking group is released by cleavage of the ribonucleotide by an RNase enzyme (FIG. 14C). After RNase cleavage of the blocking group, the adapter-flanked template nucleic acid molecule is barcoded by, e.g., a nucleic acid extension reaction.

In some embodiments, the plurality of nucleic acid barcode molecules are able to anneal to the template, but no extension products can be generated until the 3' blocking group is cleaved by the RNase enzyme.

In some embodiments, following linear amplification, DNA is purified and RNase enzyme is removed. In some instances, remaining nucleic acid barcode molecules may anneal to the template DNA during SI-PCR, but do not prime DNA polymerase because of the 3' blocking group, thus minimizing barcode exchange.

Minimizing Barcode Exchange in Ligation Barcoding

Disclosed herein, in some embodiments, are methods for nucleic acid processing, comprising, in a plurality of partitions, using nucleic acid barcode molecules from a plurality of nucleic acid barcode molecules and a plurality of nucleic acid molecules (e.g., from or derived from a cell) to generate a plurality of barcoded nucleic acid molecules, wherein the nucleic acid barcode molecules comprises a sequence, site, or region that prevents nucleic acid amplification, synthesis, and/or extension. The nucleic acid barcode molecules may be partially double-stranded (e.g., comprise a single-stranded overhang) and may additionally comprise one or more functional sequences such as a primer sequence, a primer annealing sequence, a barcode sequence, a unique molecular index, or complements of any of these sequences, and a site, sequence, or region (e.g., an abasic site, noncanonical base, a 3' blocking moiety, etc.) that may prevent amplification and/or extension of the nucleic acid barcode molecule (e.g., via an enzyme that synthesizes nucleic acid molecules off a template strand). In some cases, the nucleic acid barcode molecules may comprise a 5' overhang sequence. In some cases, the 5' overhang sequence may comprise an abasic site or a noncanonical base (e.g., uracil). The abasic site or noncanonical base (e.g., uracil) may be positioned any number of base positions (e.g., 3, 4, 5, 6, 7 or 8 base positions) in the 5' direction of the overhang sequence. In some cases, a 3' blocking moiety is used.

In some instances, the plurality of partitions is a plurality of droplets (e.g., droplet emulsion). In some instances, the plurality of partitions is a plurality of wells (e.g., a microwell array).

In some embodiments, the sequence that prevents amplification and/or extension comprises an abasic site. In some embodiments, the sequence that prevents amplification and/or extension comprises a noncanonical base, e.g., uracil. In some embodiments, the sequence that prevents amplification and/or extension comprises a 3' block, e.g., a 3' extension blocker.

In some embodiments, the plurality of barcoded nucleic acid molecules is generated by ligation of the plurality of partially double-stranded nucleic acid barcode molecules to the plurality of nucleic acid molecules.

In some embodiments, ligation-based barcode conjugation is used to barcode tagmented, adapter-flanked template DNA (see, e.g., FIG. 10B, FIG. 17, and U.S. Pat. Pub. No. 20180340169, which is hereby incorporated by reference in its entirety). In some instances, the nucleic acid barcode molecule comprises a partially double-stranded region. As used herein, the term "nucleic acid barcode molecule" may, in some instances, refer to the partially double-stranded barcode nucleic acid molecule. The barcode nucleic acid molecule may comprise an adapter sequence (e.g., an Illumina P5 sequence or a complement thereof), a barcode sequence, and a primer sequence (e.g., a sequencing primer sequence, for example an Illumina R1 or R2 sequencing primer sequence or a complement thereof). Additionally or alternatively, the barcode molecule may comprise any combination or variations of functional sequences, e.g., a spacer sequence (as described elsewhere herein), a unique molecular identifier, a binding sequence, a restriction site, etc. The nucleic acid barcode molecule may associate with the tagmented, adapter-flanked template DNA (e.g., via hybridization). In some cases, one or more sequences (e.g., a 5' overhang) on the nucleic acid barcode molecule may be complementary and/or capable of annealing to one or more sequences on the tagmented, adapter-flanked template DNA. In some cases, the tagmented adapter-flanked template DNA may be treated with an enzyme, e.g., T4 polynucleotide kinase, to phosphorylate the 5' ends. The nucleic acid barcode molecule may then be ligated to the tagmented, adapter-flanked template DNA using an enzyme, e.g., a ligase (e.g., T4 DNA ligase) to generate a barcoded nucleic acid molecule. In some examples, the nucleic acid barcode molecule is coupled to a solid support. In some instances, the solid support is a bead. In some embodiments, the solid support is a gel bead as described elsewhere herein. In some instances, the nucleic acid barcode molecules are releasably attached to the solid support as described elsewhere herein.

Figure 18:
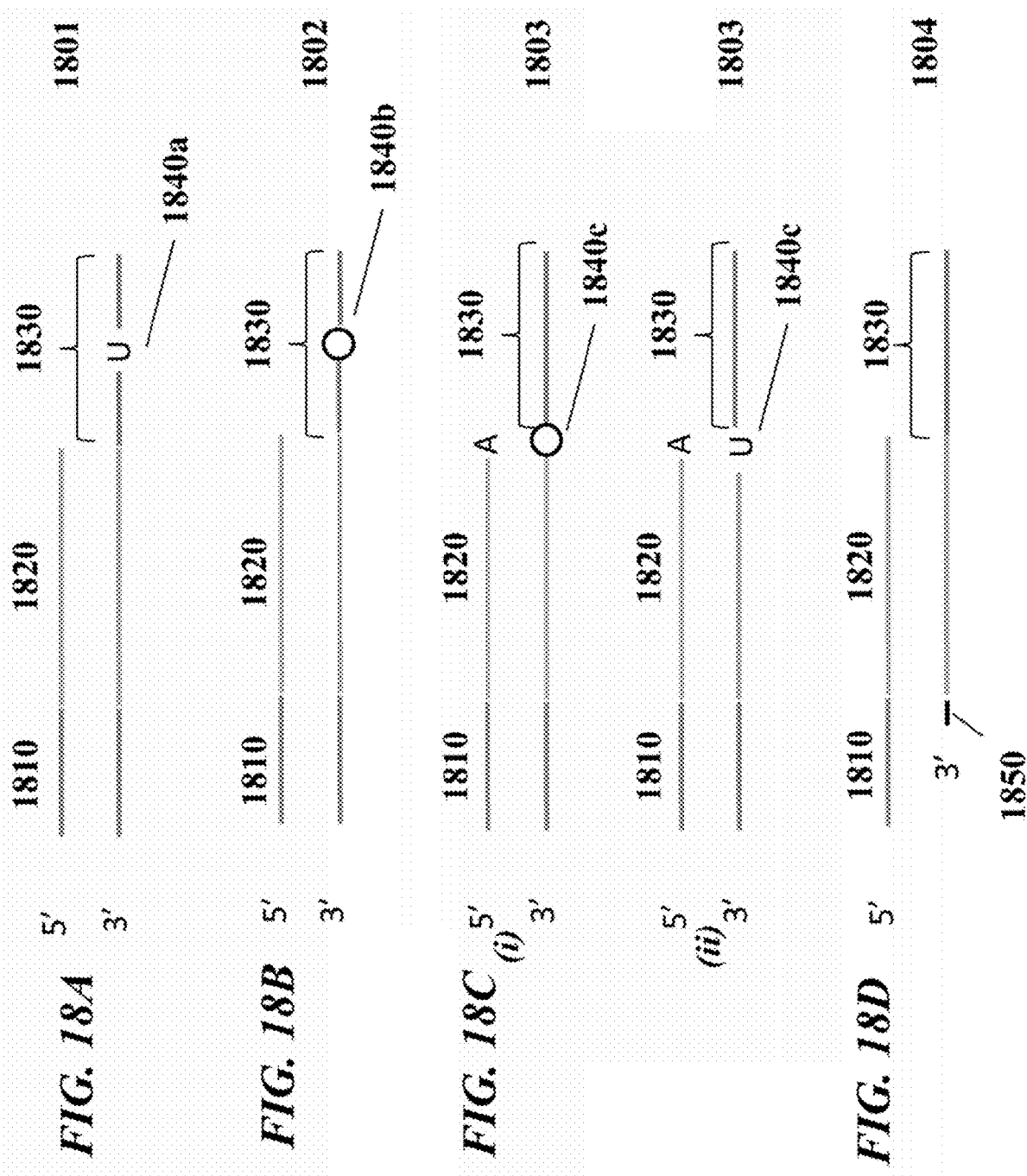
FIGS. 18 A-D show schematics of exemplary designs of nucleic acid barcode molecules that may prevent barcode extension.

FIG. 18A shows schematically an exemplary nucleic acid barcode molecule 1801 that may prevent downstream amplification and/or extension of the nucleic acid barcode molecule 1801 (e.g., a polymerase synthesizing a strand off an overhang sequence or template strand). The nucleic acid barcode molecule may be partially-double-stranded (e.g., comprise a single-stranded overhang). The nucleic acid barcode molecule 1801 may comprise an adapter sequence 1810 (e.g., a P5 sequence), a barcode sequence 1820, and a primer sequence 1830 (e.g., a R1 sequencing primer sequence), or a complement of any of these sequences. The primer sequence 1830 (e.g., R1 sequence) or complement thereof of the nucleic acid barcode molecule 1801 may be a single-stranded overhang sequence (e.g., a 5' overhang) and may be at least partially complementary and/or capable of annealing to a sequence of the adapter-flanked template nucleic acid fragment and may comprise a base pair, a site, or a sequence that prevents amplification and/or extension 1840a (e.g., a noncanonical base (e.g. uracil as shown in FIG. 18A), an oxidized base pair, a spacer (e.g., C3 spacer) or a methylated base pair). In cases where a uracil is used, the uracil may be placed in any position in sequence 1830, e.g., in position 1, 2, 3, 4, 5, 6, 7, 8, 9, etc. following the double stranded junction. In some cases, the nucleic acid barcode molecule comprising the uracil may be treated with an enzyme, e.g., uracil-DNA-glycosylase to generate an abasic site 1840b. In some embodiments, the abasic site (also known as a tetrahydrofuran (THF) site or apurinic/apyrimidinic (AP) site) is generated though the chemical synthesis of the oligonucleotide primer. In some embodiments, the chemically synthesized abasic site may contain a dideoxytetrahydrofuran, 1'-ribotetrahydrofuran, or 2'-ribotetrahydrofuran (also known as an Abasic II site). FIG. 18B shows schematically another exemplary nucleic acid barcode molecule 1802 that may prevent downstream amplification and/or extension of the nucleic acid barcode molecule 1802. The nucleic acid barcode molecule may be partially-double-stranded. The nucleic acid barcode molecule 1802 may comprise adapter sequence 1810 (e.g., a P5 sequence), a barcode sequence 1820, and a primer sequence 1830 (e.g., a R1 sequencing primer sequence), or a complement of any of these sequences. The primer sequence 1830 (e.g., a R1 sequence), or complement thereof, may be a single-stranded overhang sequence (e.g., 5' overhang) at least partially complementary and/or capable of annealing to a sequence of the adapter-flanked template nucleic acid fragment and may comprise a sequence, site, or region that prevents amplification and/or extension, e.g., an abasic site 1840b. The abasic site 1840b may be placed in any position in sequence 1830, e.g., in position 1, 2, 3, 4, 5, 6, 7, 8, 9, etc. following the double stranded junction. FIG. 18C shows schematically an exemplary nucleic acid barcode molecule 1803 that may prevent downstream amplification and/or extension of the nucleic acid barcode molecule 1803. The nucleic acid barcode molecule may be partially-double-stranded. The nucleic acid barcode molecule 1803 may comprise an adapter sequence 1810 (.g., a P5 sequence), a barcode sequence 1820, and a primer sequence 1830 (e.g., a R1 sequencing primer sequence), or a complement thereof of any of these sequences. The primer sequence 1830 or complement thereof of the nucleic acid barcode molecule 1803 may be an overhang sequence (e.g., 5' overhang sequence) and may be at least partially complementary to a sequence of the adapter-flanked template nucleic acid fragment and may comprise a sequence, site, or region that prevents amplification and/or extension, e.g., an abasic site 1840c (Panel i) or a noncanonical base (e.g., uracil, Panel ii). The uracil or abasic site 1840c may be placed at the double stranded junction (e.g., at the last [3' end] base position of the barcode sequence 1820 [denoted with "A"] on the complementary [bottom] strand). FIG. 18D shows schematically another exemplary nucleic acid barcode molecule 1804 that may prevent downstream amplification and/or extension of the nucleic acid barcode molecule 1804. The nucleic acid barcode molecule may be partially-double-stranded. The nucleic acid barcode molecule 1804 may comprise an adapter sequence 1810 (e.g., a P5 sequence), a barcode sequence 1820, and a primer sequence 1830 (e.g., a R1 sequencing primer sequence), or a complement thereof of any of these sequences. The primer sequence 1830, or complement thereof, of the nucleic acid barcode molecule 1804 may be an overhang sequence (e.g., a 5' overhang sequence) and may be at least partially complementary to a sequence of the adapter-flanked template nucleic acid fragment. One of the strands (e.g., the bottom strand) of the nucleic acid barcode molecule 1804 may comprise a sequence that prevents amplification and/or extension, e.g., a 3' blocking group 1850, which may block extension. The 3' extension blocker may be a 3' C3 spacer, a dideoxynucleotide, an inverted nucleotide, an amino or phosphate group, etc.

In some embodiments, the 3' blocking group of the compositions disclosed herein is at a 3' terminus of the blocking oligonucleotide. In some embodiments, the 3' blocking group of the compositions disclosed herein is a 2'-3'-dideoxycytosine (ddC). In some embodiments, the 3' blocking group of the compositions disclosed herein is a 2'-5' linked nucleoside. In some embodiments, the 3' blocking group of the compositions disclosed herein is a 3' C3 spacer. In some embodiments, the 3' blocking group of the compositions disclosed herein is an amino-modified C6. In some embodiments, the 3' blocking group of the compositions disclosed herein is an inverted deoxythymidine (dT). In some embodiments, the 3' blocking group of the compositions disclosed herein is a 3' amino modified nucleotide. In some embodiments, the 3' blocking group of the compositions disclosed herein is a 3' phosphate group. In some embodiments, the 3' blocking group of the compositions disclosed herein is a 2'-5' linked nucleoside, wherein the 2'-5' linked nucleoside is a 3'-deoxythymidine (3'-dT). In some instances, the 2'-5' linked nucleoside of the compositions disclosed herein is a 3'-deoxycytidine (3'-dC). In some instances, the 2'-5' linked nucleoside of the compositions disclosed herein is a 3'-deoxyadenosine (3'-dA). In some instances, the 2'-5' linked nucleoside of the compositions disclosed herein is a 3'-deoxyguanosine (3'-dG).

The blocking oligonucleotides disclosed herein are also useful in preventing unwanted interactions in a variety of nucleic acid based reactions. For example, the blocking oligonucleotides disclosed herein may be utilized to block, inhibit, or otherwise alter the rate of a PCR reaction (e.g., in situations where (1) a purification step cannot be performed or is unideal or (2) to minimize a PCR reaction primed from one or more specific primers or primer sets in a sample). In some cases, the blocking oligonucleotides prevent nucleic acid extension or ligation.

A barcode molecule comprising a sequence that prevents amplification and/or extension may be useful in preventing barcode exchange reactions, e.g., those shown in FIG. 12B. For example, after barcoded, adapter-flanked template nucleic acid molecules are removed from partitions and combined in a bulk sample index PCR (SI-PCR) reaction, any remaining unincorporated nucleic acid barcode molecules may be subjected to undesirable amplification reactions (e.g., the barcode exchange reactions described herein). However, a part of the nucleic acid barcode molecule (e.g., one of the strands) which comprises a sequence that prevents amplification and/or extension may not be amplified, and thus generation of extra/carry-over double-stranded barcode molecules is minimized. Since the extra barcode molecules may compete with the primers utilized for SI-PCR of the adapter-flanked template nucleic acid molecules or product thereof and lead to a high rate of barcode exchange, a method using barcode molecules comprising a sequence that prevents amplification and/or extension may significantly reduce barcode exchange (see, e.g., FIG. 20).

Computer Systems

Figure 9:
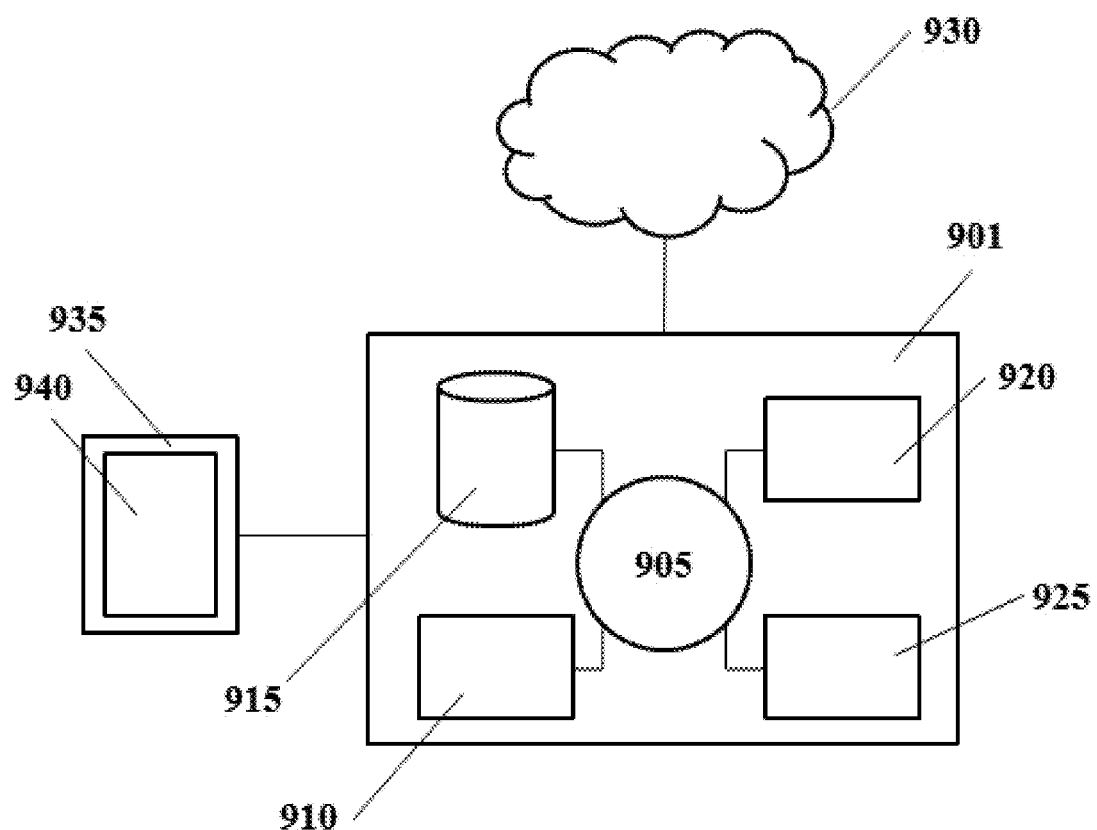
FIG. 9 shows a computer system that is programmed or otherwise configured to implement methods provided herein.

The present disclosure provides computer systems that are programmed to implement methods of the disclosure. FIG. 9 shows a computer system 901 that is programmed or otherwise configured to, e.g., (i) control a microfluidics system (e.g., fluid flow), (ii) sort occupied droplets from unoccupied droplets, (iii) polymerize droplets, (iv) perform sequencing applications, (v) generate and maintain a library of DNA or cDNA fragments, and/or (vi) analyze areas of accessible chromatin. The computer system 901 can regulate various aspects of the present disclosure, e.g., e.g., regulating fluid flow rate in one or more channels in a microfluidic structure, regulating polymerization application units, regulating conditions for certain reactions described herein. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, e.g., cache, other memory, data storage and/or electronic display adapters. The memory 910, storage unit 915, interface 920 and peripheral devices 925 are in communication with the CPU 905 through a communication bus (solid lines), e.g., a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, e.g., cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, e.g., the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, e.g., an integrated circuit. One or more other components of the system 901 can be included in the circuit. In some cases, the circuit is an application specific integrated circuit (ASIC).

The storage unit 915 can store files, e.g., drivers, libraries and saved programs. The storage unit 915 can store user data, e.g., user preferences and user programs. The computer system 901 in some cases can include one or more additional data storage units that are external to the computer system 901, e.g., located on a remote server that is in communication with the computer system 901 through an intranet or the Internet.

The computer system 901 can communicate with one or more remote computer systems through the network 930. For instance, the computer system 901 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, e.g., on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, e.g., the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, e.g., memory (e.g., read-only memory, random-access memory, flash memory) or a hard disk. "Storage" type media can include any or all of the tangible memory of the computers, processors or the like, or associated modules thereof, e.g., various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, e.g., used across physical interfaces between local devices, through wired and optical landline networks and over various air-links. The physical elements that carry such waves, e.g., wired or wireless links, optical links or the like, also may be considered as media bearing the software. As used herein, unless restricted to non-transitory, tangible "storage" media, terms e.g., computer or machine "readable medium" refer to any medium that participates in providing instructions to a processor for execution.

Hence, a machine readable medium, e.g., computer-executable code, may take many forms, including but not limited to, a tangible storage medium, a carrier wave medium or physical transmission medium. Non-volatile storage media include, for example, optical or magnetic disks, e.g., any of the storage devices in any computer(s) or the like, e.g., may be used to implement the databases, etc. shown in the drawings. Volatile storage media include dynamic memory, e.g., main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves e.g., those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, results of sequencing analysis, correlating sequencing reads to areas with barcode exchange occurrences, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, perform sequencing reactions, correlate sequencing reads with barcode exchange occurrences, etc.

Devices, systems, compositions and methods of the present disclosure may be used for various applications, e.g., processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1. Generation of Barcoded Nucleic Acid Fragments Using Bulk Tagmentation and Barcoding by Linear Amplification in Partitions Nuclei are harvested in bulk from cells in a cell population of interest in a manner that substantially maintains native chromatin organization. Alternatively, cells are permeabilized, allowing the transposase-nucleic acid complex to gain access to the nucleus. In some cases, the cell may be incorporated in a cell bead as described elsewhere herein. Permeabilized nuclei (or permeabilized cells) are then incubated in the presence of a transposase-nucleic acid complex to generate adapter-flanked nucleic acid fragments (e.g., of genomic DNA, such as genomic DNA in chromatin).

Nuclei (or cells) comprising the adapter-flanked template nucleic acid fragments are then partitioned into a plurality of partitions (e.g., a plurality of droplets or a plurality of wells) such that at least some partitions comprise (1) a single nucleus (or cell) comprising the adapter-flanked template nucleic acid fragments; and (2) a plurality of single-stranded barcode oligonucleotide molecules comprising a transposon end sequence (ME), a Read1 sequence (R1), or a portion thereof, a barcode sequence (BC), and a P5 adapter sequence (P5). In some embodiments, the single-stranded barcode oligonucleotide molecules are attached to a gel bead and partitioned such that at least some partitions comprise (1) a single nucleus (or cell) comprising the adapter-flanked template nucleic acid fragments and (2) a single gel bead. In addition to the aforementioned components, in some embodiments, the plurality of partitions further comprises reagents (e.g., enzymes and buffers) that facilitate the reactions described below.

Single nucleus containing partitions are then subjected to conditions to release the adapter-flanked template nucleic acid fragments from the nuclei. After the adapter-flanked template nucleic acid fragments are released, gaps from the transposition reaction are filled with a suitable enzyme. In certain embodiments, where barcode oligonucleotides are attached to a gel bead, partitions are subjected to conditions to cause release of the barcode oligonucleotide molecules from the gel bead (e.g., depolymerization of gel beads, for example, using a reducing agent e.g., DTT). Gap-filled adapter-flanked template nucleic acid fragments are then subjected to a linear amplification reaction using the single-stranded barcode oligonucleotide molecules as primers to produce barcoded, adapter-flanked template nucleic acid fragments. See FIG. 11.

The barcoded, adapter-flanked template nucleic acid fragments are then released from the partitions and processed in a bulk sample indexing polymerase chain reaction (SI-PCR) to complete library preparation for next generation high throughput sequencing (e.g., to add sample index (SI) sequences (e.g., i7) and/or further adapter sequences (e.g., P7)). In some instances, the blocking oligonucleotides of the present disclosure are ligated to the barcoded, adapter-flanked template nucleic acid fragments prior to bulk processing (e.g., SI-PCR) to prevent barcode exchange, as shown in FIG. 12A. In some examples, the ribonucleotide-containing barcode molecules containing a 3' blocking group from the present disclosure are used to prevent barcode exchange prior to bulk processing (i.e., SI-PCR), as shown in FIG. 14. The fully constructed library is then sequenced according to a suitable next-generation sequencing protocol (e.g., Illumina sequencing).

Example 2. Generation of Barcoded Nucleic Acid Fragments Using Tagmentation and Barcoding by Linear Amplification in Partitions Cells from a cell population of interest (or intact nuclei from cells in a cell population of interest) are partitioned into a plurality of partitions, or incorporated in a cell bead and partitioned such that at least some partitions comprise (1) a single cell (or a single nucleus), or a single cell bead, comprising a template nucleic acid; and (2) a plurality of single-stranded barcode oligonucleotide molecules comprising a transposon end sequence (ME), a Read1 sequence (R1), a barcode sequence (BC), and a P5 adapter sequence (P5). In some embodiments, the single-stranded barcode oligonucleotide molecules are attached to a gel bead and partitioned such that at least some partitions comprise (1) a single cell (or a single nucleus) and (2) a single gel bead. In addition to the aforementioned components, in some embodiments, the plurality of partitions further comprises reagents (e.g., enzymes and buffers) that facilitate the reactions described below.

After partitioning into partitions, the single cells (or nuclei) are lysed to release the template genomic DNA in a manner that substantially maintains native chromatin organization. In certain embodiments, where barcode oligonucleotides are attached to a gel bead, partitions are subjected to conditions to cause release of the barcode oligonucleotide molecules from the gel bead (e.g., depolymerization of gel beads, for example, using a reducing agent e.g., DTT). Partitions are then subjected to conditions to generate a transposase-nucleic acid complex. Alternatively, in some embodiments, a plurality of pre-formed transposase-nucleic acid complexes are partitioned into the plurality of partitions. Partitions are then subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

Samples are then processed generally as described in Example 1. After tagmentation, gaps from the transposition reaction are filled with a suitable gap-filling enzyme. Gap-filled adapter-flanked template nucleic acid fragments are then subjected to a linear amplification reaction using the single-stranded barcode oligonucleotide molecules as primers to produce barcoded, adapter-flanked template nucleic acid fragments.

The barcoded, adapter-flanked template nucleic acid fragments are then released from the partitions and processed in bulk to complete library preparation for next generation high throughput sequencing (e.g., to add sample index (SI) sequences (e.g., i7) and/or further adapter sequences (e.g., P7)). In some instances, the blocking oligonucleotide of the present disclosure is ligated to the barcoded, adapter-flanked template nucleic acid fragments prior to bulk processing (reaction (e.g., SI-PCR) to prevent barcode exchange, as shown in FIG. 12A. In some examples, the ribonucleotide-containing barcode molecules containing a 3' blocking group from the present disclosure are used to prevent barcode exchange prior to bulk processing (i.e., SI-PCR), as shown in FIG. 14. The fully constructed library is then sequenced according to a suitable next-generation sequencing protocol (e.g., Illumina sequencing).

Example 3. Hairpin Cap Prevents Amplification Via PCR

Figure 15A:
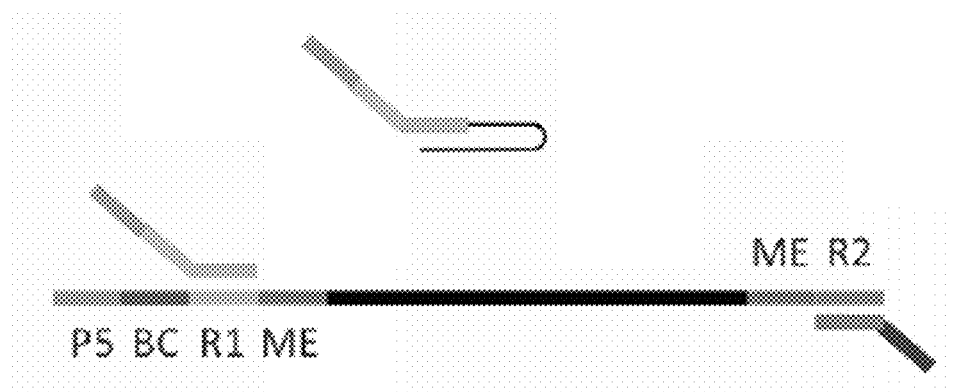
FIGS. 15A and 15B show representative results of amplification reactions using blocking oligonucleotides.
Figure 15B:
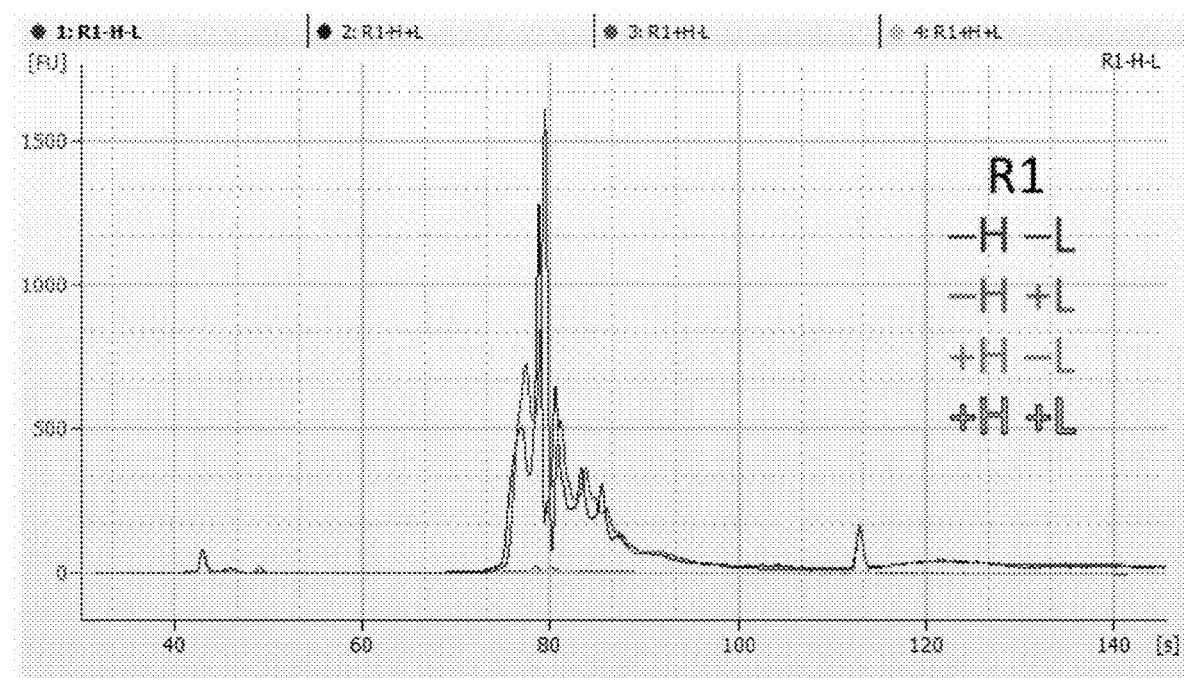

The blocking oligonucleotides of the present disclosure were tested to determine if they can successfully block polymerase chain reaction (PCR). A fragment of DNA similar to the adapter-flanked template nucleic acid molecules disclosed herein (see FIG. 11) was generated and amplified using primers complementary to the R1 and R2 sequences in the adapter-flanked nucleic acid molecules see FIG. 15A. Prior to PCR, the sample was incubated with ("+H") or without ("−H") blocking oligonucleotides, and with ("+L") or without ("−L") DNA ligase. Following PCR, reactions were cleaned up and run on a Bioanalyzer to quantify the DNA (FIG. 15B). As seen in FIG. 15B, when the blocking oligo was not included ("−H"), PCR products were readily detected, as indicated by the blue and red peaks on the graph. However, when the blocking oligonucleotide was included, even in the absence of DNA ligase, PCR products were substantially reduced, as indicated by the absence of peaks in the green and cyan lines on the graph on FIG. 15B. Overall, the results confirm that the blocking oligonucleotides of the present disclosure can inhibit PCR reactions and function to reduce barcode exchange reactions. Furthermore, as seen by the reactions including a blocking oligonucleotide but no DNA ligase, hybridization of the blocking oligonucleotide to a primer sequence can be sufficient to inhibit PCR and ligation of the blocking oligonucleotide to the primer may not be strictly necessary.

Example 4. Hairpin Cap Reduces Barcode Exchange

Figure 16:
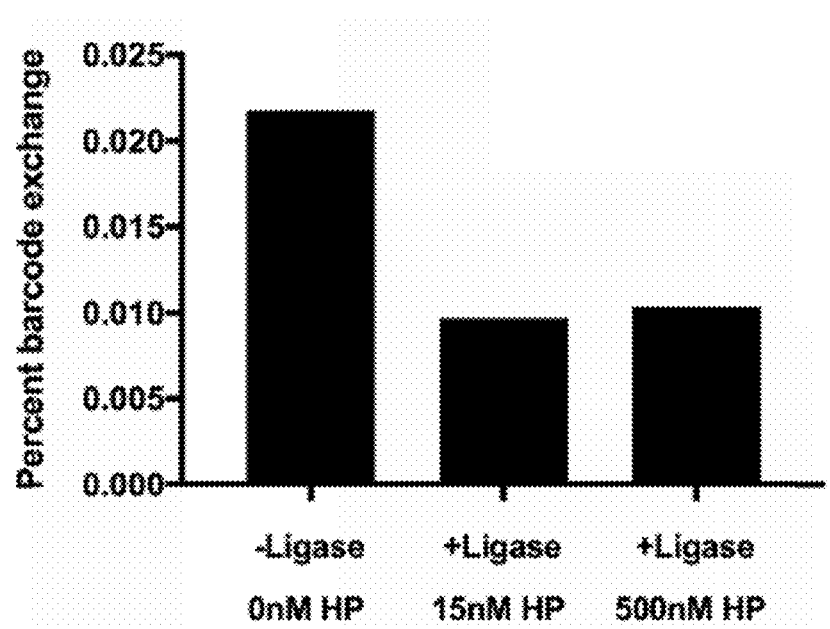
FIG. 16 shows representative data showing barcode exchange percentage using blocking oligonucleotides.

The blocking oligonucleotides of the present disclosure were tested to determine if they can successfully reduce barcode exchange during SI-PCR reactions on barcoded, adapter-flanked template nucleic acid fragments. To this end, an exogenous barcode nucleic acid molecule (containing a barcode sequence different than the barcode sequences used to barcode the template nucleic acid fragments) was spiked-into a SI-PCR reaction following linear amplification (see FIG. 11 generally). As such, the only way for the exogenous barcode sequence to be present in the final library is by a barcode exchange event as described herein. Following linear amplification, SI-PCR reactions were setup with a constant concentration of the exogenous barcode and two different concentrations of a blocking oligonucleotide ("HP"—15 nM and 500 nM) and DNA ligase ("+Ligase"). A negative control reaction was setup without a blocking oligonucleotide ("OnM HP") and without DNA ligase ("−Ligase"). The final library products were then sequenced and the fraction of reads that contained the exogenous barcode were calculated. Results show that the frequency of barcode exchange dropped by ~50% and appeared to be independent of the concentration of blocking oligonucleotide utilized (FIG. 16).

Example 5. Generation of Barcoded Nucleic Acid Fragments Using Bulk Tagmentation and Barcoding by Ligation in Partitions Nuclei are harvested in bulk from cells in a cell population of interest in a manner that substantially maintains native chromatin organization. Alternatively, cells are permeabilized, allowing the transposase-nucleic acid complex to gain access to the nucleus. Cells may be incorporated in a cell bead as described elsewhere herein. Permeabilized nuclei (or permeabilized cells) are then incubated in the presence of a transposase-nucleic acid complex to generate adapter-flanked nucleic acid fragments (e.g., of genomic DNA, such as genomic DNA in chromatin).

Nuclei (or cells or cell beads) comprising the adapter-flanked template nucleic acid fragments are then partitioned into a plurality of partitions (e.g., a plurality of droplets or a plurality of wells) such that at least some partitions comprise (1) a single nucleus (or cell or cell bead) comprising the adapter-flanked template nucleic acid fragments; and (2) a plurality of partially double-stranded nucleic acid barcode molecules comprising a transposon end sequence, a Read1 sequence (R1), or a portion thereof, a barcode sequence (BC), and a P5 adapter sequence (P5). In some embodiments, the partially double-stranded nucleic acid barcode molecules are attached to a gel bead and partitioned such that at least some partitions comprise (1) a single nucleus (or cell or cell bead) comprising the adapter-flanked template nucleic acid fragments and (2) a single gel bead. In addition to the aforementioned components, in some embodiments, the plurality of partitions further comprises reagents (e.g., enzymes and buffers) that facilitate the reactions described below.

Single nucleus containing partitions are then subjected to conditions to release the adapter-flanked template nucleic acid fragments from the nuclei. After the adapter-flanked template nucleic acid fragments are released, the 5' ends are treated with an enzyme, e.g. a T4 polynucleotide kinase, to phosphorylate the 5'ends of the adapter-flanked template nucleic acid fragments. In certain embodiments, where barcode oligonucleotides are attached to a gel bead, partitions are subjected to conditions to cause release of the nucleic acid barcode molecules from the gel bead (e.g., depolymerization of gel beads, for example, using a reducing agent e.g., DTT). The barcode oligonucleotide molecules may be partially double-stranded and may associate with (e.g., anneal to) the 5'-phosphorylated adapter-flanked template nucleic acid fragments. The barcode oligonucleotide molecules may then be ligated to the 5'-phosphorylated adapter-flanked template nucleic acid fragments using an enzyme, e.g., a ligase (e.g. T4 DNA ligase) to generate a barcoded nucleic acid molecule. See, e.g., FIG. 17. The partition is then broken or disrupted, and the barcoded nucleic acid molecule is subjected to conditions sufficient to gap fill the gaps introduced from tagmentation as well as add additional sequences, e.g., a P7 sequence and i7 sequence (e.g., subjected to SI-PCR for library preparation and sequencing).

Figure 19:
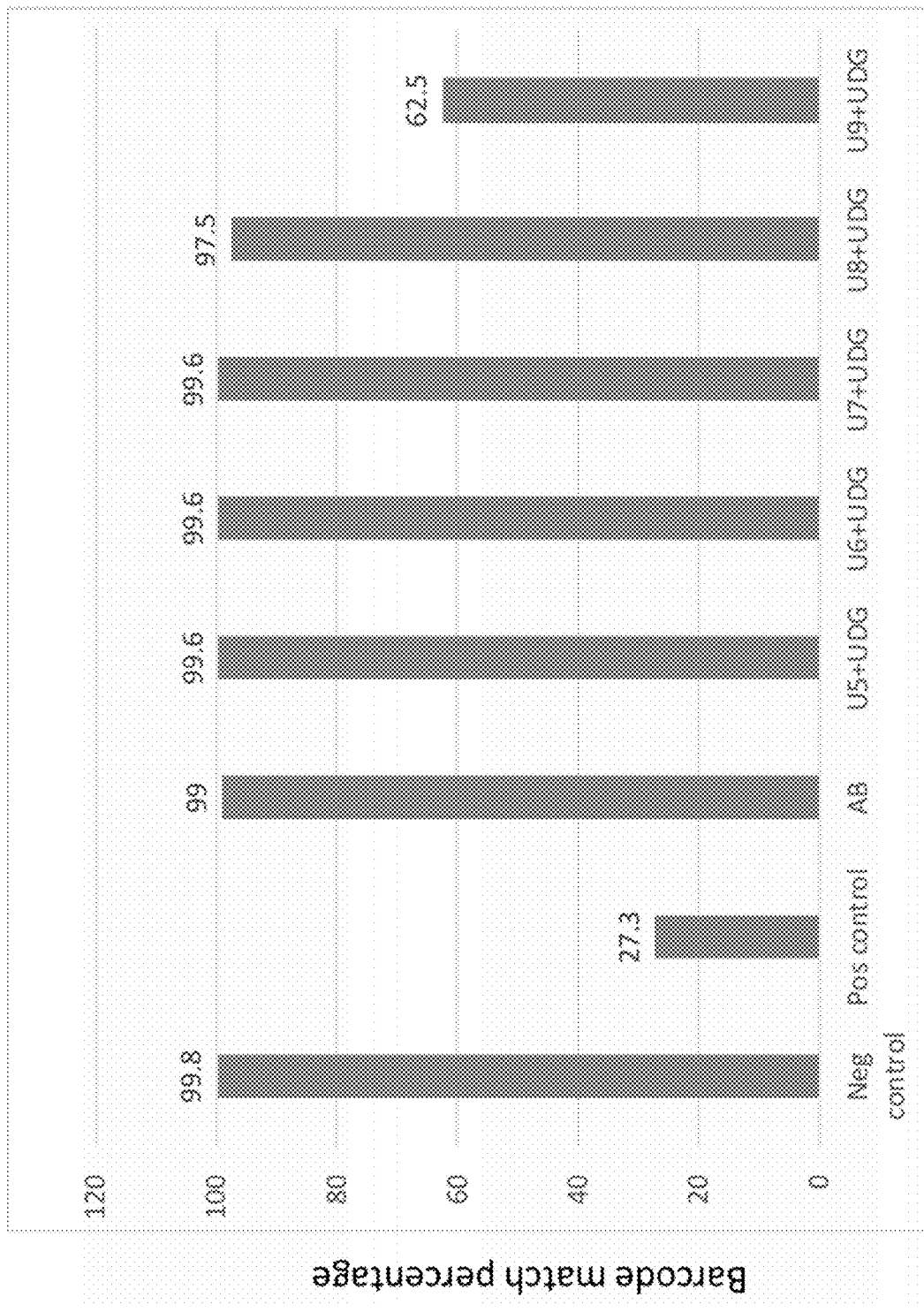
FIG. 19 shows representative data showing barcode match percentage using a nucleic acid molecule comprising a noncanonical base, e.g., uracil.

Example 6. Positioning of Uracil in a Partially Double-Stranded Barcode Molecule Prevents Barcode Exchange To test barcode exchange, partially-double stranded nucleic acid barcode molecules comprising a uracil or an abasic site (e.g., as depicted in FIGS. 18A-C) were spiked into a barcoded library and the amount of barcode match (barcode correspondence) was determined. Briefly, a PCR reaction was performed with (1) an extraneous partially double-stranded barcode molecule; and (2) one of 4 DNA templates each with the following structure P5-BC-R1-insert-R2-P7 and having the same sequence except for the barcode (see Table 1; barcode sequence in bold, insert underlined). After the PCR, the reaction products were purified, sequenced, and the number of reads associated with the original 4 barcodes were determined as a barcode match percentage (FIG. 19). The negative control reaction contained no spiked-in extraneous barcode while positive control contained a spiked-in barcode that did not contain any uracil or abasic site. For certain reactions, a spiked-in barcode molecule contained a uracil or abasic site at select positions. The uracil or abasic moiety was placed in a variety of positions in the single-stranded portion of the barcode molecule (e.g., at various locations within the R1 primer sequence on the bottom strand comprising the 5' overhang sequence) and treated with uracil-DNA-glycosylase (UDG) to generate an abasic site. The uracil was positioned 3, 4, 5, 6, 7, 8, or 9 bases away (in the 5' direction) from the double-stranded junction on the strand comprising the 5' overhang sequence.

As seen in FIG. 19, the percentage of barcode correspondence is plotted as bars for each condition tested. An abasic ("AB") site at position 5 away (in the 5' direction on the strand comprising the 5' overhang sequence) from the junction resulted in about 99% barcode correspondence. Similarly, a uracil at positions 5, 6, 7, or 8 away (in the 5' direction on the strand comprising the 5' overhang sequence) from the junction, followed by UDG treatment resulted in barcode correspondence of greater than 95% (99.6% at positions 5, 6, and 7, 97.5% at position 8). Likewise, uracil or an abasic site positioned 3 or 4 nucleotides away (in the 5' direction on the strand comprising the 5' overhang sequence) from the double-stranded junction, followed by UDG treatment resulted in high barcode correspondence (data not shown). However, uracil positioned 9 bases away (in the 5' direction on the strand comprising the 5' overhang sequence) from the double-stranded junction resulted in a higher degree of barcode exchange (62.5% barcode match). Overall, the results confirm that the incorporation of uracil followed by UDG treatment or abasic sites in the 5' overhang sequence of nucleic acid barcode molecules of the present disclosure can reduce barcode exchange reactions using the methods described herein.

TABLE 1

| Sequences used in spike-in reactions. | |
|---|---|
| Template 1 (5'-3') | AATGATACGGCGACCACCGAGATCTACACGACTA GTGTACCCACGTCGTCGGCAGCGTCAGATGTGTA TAAGAGACAGATGGGTAGCTCTCACCATCATCAT CATCACTCTAGCGGTCTGGTCCCTCGCGGTAGCC ACATGCCACGTAAAATGTATAGCTGTGATTTTGA GACTACGACGAAAGTTGAAGATTGCCGTGTGTGG GCGTATGGTTACATGAATATTGAAGATCACTCCG AGTATAAGATTGGCAATAGCCTGGATGAATTCAT GGCGTGCTGTCTCTTATACACATCTCCGAGCCCA CGAGAC (SEQ ID NO: 1) |
| Template 2 (5'-3') | AATGATACGGCGACCACCGAGATCTACACATCTG AAGACATCGTCTCGTCGGCAGCGTCAGATGTGTA TAAGAGACAGATGGGTAGCTCTCACCATCATCAT CATCACTCTAGCGGTCTGGTCCCTCGCGGTAGCC ACATGCCACGTAAAATGTATAGCTGTGATTTTGA GACTACGACGAAAGTTGAAGATTGCCGTGTGTGG GCGTATGGTTACATGAATATTGAAGATCACTCCG AGTATAAGATTGGCAATAGCCTGGATGAATTCAT |

TABLE 1-continued

Sequences used in spike-in reactions.

| | |
|---|---|
| | GGCGTGCTGTCTCTTATACACATCTCCGAGCCCA CGAGAC (SEQ ID NO: 2) |
| Template 3 (5'-3') | AATGATACGGCGACCACCGAGATCTACACTCAGC GTCTTCCATGATCGTCGGCAGCGTCAGATGTGTA TAAGAGACAGATGGGTAGCTCTCACCATCATCAT CATCACTCTAGCGGTCTGGTCCCTCGCGGTAGCC ACATGCCACGTAAAATGTATAGCTGTGATTTTGA GACTACGACGAAAGTTGAAGATTGCCGTGTGTGG GCGTATGGTTACATGAATATTGAAGATCACTCCG AGTATAAGATTGGCAATAGCCTGGATGAATTCAT GGCGTGCTGTCTCTTATACACATCTCCGAGCCCA CGAGAC (SEQ ID NO: 3) |
| Template 4 (5'-3') | AATGATACGGCGACCACCGAGATCTACACCGTAT CCTCAGGTCAGTCGTCGGCAGCGTCAGATGTGTA TAAGAGACAGATGGGTAGCTCTCACCATCATCAT CATCACTCTAGCGGTCTGGTCCCTCGCGGTAGCC ACATGCCACGTAAAATGTATAGCTGTGATTTTGA GACTACGACGAAAGTTGAAGATTGCCGTGTGTGG GCGTATGGTTACATGAATATTGAAGATCACTCCG AGTATAAGATTGGCAATAGCCTGGATGAATTCAT GGCGTGCTGTCTCTTATACACATCTCCGAGCCCA CGAGAC (SEQ ID NO: 4) |
| Spike-in top strand (5'-3') | AATGATACGGCGACCACCGAGATCT ACACGAGCATGAGGTAGACT (SEQ ID NO: 5) |
| Spike-in bottom strand positive control (5'-3') | GACGCTGCCGACGAAGTCTACCTCATGCTCG TGTAGATCTCGGTGGTCGCCGTATCATT (SEQ ID NO: 6) |

Figure 20:
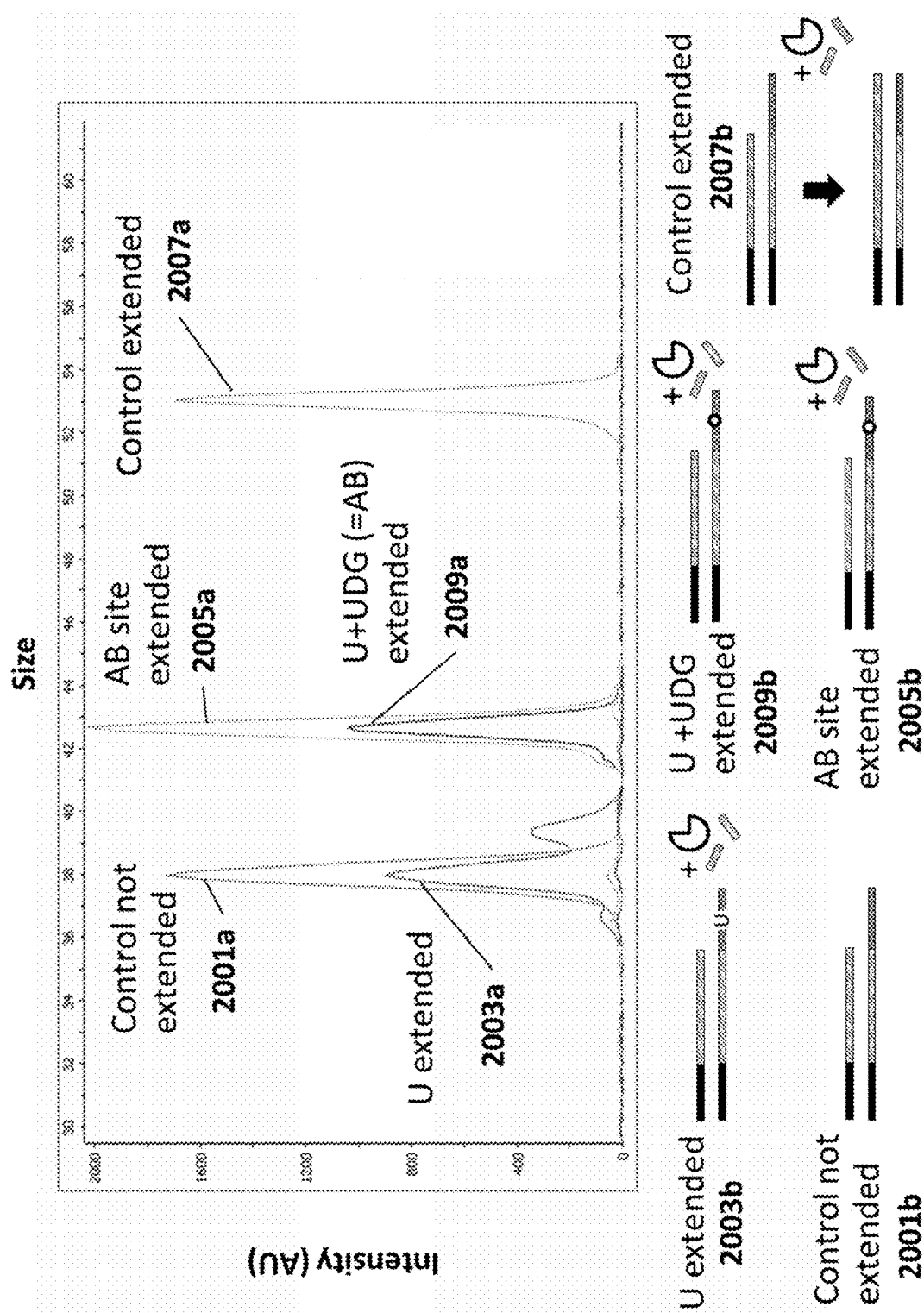
FIG. 20 shows representative data showing prevention of extension using a nucleic acid molecule comprising a non-canonical base, e.g., uracil or abasic site.

Example 7. Incorporation of a Sequence that Prevents Amplification in the Barcode Molecule Prevents Extension The incorporation of a sequence to prevent amplification in the nucleic acid barcode molecule was tested to determine if such a method can successfully prevent extension of the nucleic acid barcode molecule. A partially double-stranded nucleic acid molecule (e.g., as depicted in FIG. 18A) comprising a uracil moiety or an abasic site was used as the barcode molecule. The uracil moiety was positioned 5 bases after the double stranded junction. The nucleic acid barcode molecules comprising a uracil, the nucleic acid barcode molecules comprising an abasic site, the nucleic acid barcode molecules comprising a uracil treated with UDG (and thus comprising an abasic site) were subjected to an extension reaction. The assay is performed as follows: a 5'-FAM-labeled (fluorescein) top strand and a control/uracil/abasic site containing bottom strand (see Table 2) were annealed to each other and incubated with a polymerase (NEBNext High Fidelity 2xPCR master mix) for 5 minutes at 72° C. The reaction was then quenched with EDTA and loaded on a capillary electrophoresis machine for analysis. In some groups, prior to extension, the nucleic acid barcode molecule comprising the uracil was treated uracil-DNA-glycosylase (UDG) to generate an abasic site. FIG. 20 shows exemplary data from such an experiment. In FIG. 20, a chromatogram from capillary electrophoresis is shown. Along the x-axis is the size of the nucleic acid molecule in basepairs while the y-axis depicts fluorescent signal intensity in AU (absorbance units). As can be seen, the positive control 2007a ("control extended"—no uracil or abasic site, as schematically shown in 2007b) nucleic acid molecule was extended and resulted in a detectable peak corresponding to an extended molecule ~53 nucleotides in length. In contrast, the negative control 2001a("Control not extended" as schematically shown in 2001b) resulted in a detectable peak corresponding to an unextended molecule ~38 nucleotides in length. The uracil, non-UDG treated group 2003a (schematically shown in 2003b) that was subjected to extension had a similar length to the non-extended control group 2001a. Following extension, both the uracil/UDG treated group 2009a (schematically shown in 2009b) and the abasic group 2005a (schematically shown in 2005b) resulted in a detectable peak corresponding to a molecule ~43 nucleotides in length (uracil or abasic site 5 nucleotides after the double stranded junction). Although not shown, inclusion of uracil or an abasic site at the double-stranded junction, or at positions 1 or 2 after the double stranded junction were also effective at inhibiting extension. Overall, the results confirm that the incorporation of uracil or abasic sites in a nucleic acid barcode molecule can inhibit extension of the nucleic acid molecule and, by implication, reduce unwanted events of barcode exchange.

TABLE 2

Sequences used in extension reactions.

| | |
|---|---|
| Top Strand (5'-3') | AATGATACGGCGACCACCGAGAT CTACACGAGCATGAGGTAGACT (SEQ ID NO: 5) |
| Bottom Strand-Control (3'-5') | TTACTATGCCGCTGGTGGCTCTA GATGTGCTCGTACTCCATCTGAA GCAGCCGTCGCAG (SEQ ID NO: 6) |
| Bottom Strand-Uracil (3'-5') | TTACTATGCCGCTGGTGGCTCTA GATGTGCTCGTACTCCATCTGAA GCA/U/CCGTCGCAG (SEQ ID NO: 7) |
| Bottom Strand-Abasic "idSp" (3'-5') | TTACTATGCCGCTGGTGGCTCTA GATGTGCTCGTACTCCATCTGAA GCA/idSp/CCGTCGCAG (SEQ ID NO: 8) |

What is claimed is:

1. A method for nucleic acid processing, comprising:
   (a) contacting, in a bulk solution, a plurality of biological particles comprising template nucleic acid molecules with a plurality of transposase complexes comprising an adapter sequence to generate, from said template nucleic acid molecules, a plurality of adapter-flanked fragments, wherein said plurality of biological particles is a plurality of cells or a plurality of cell nuclei;
   (b) partitioning said plurality of biological particles into a plurality of partitions, wherein a partition of said plurality of partitions comprises:
      (i) a biological particle of said plurality of biological particles, wherein said biological particle comprises an adapter-flanked fragment of said plurality of adapter-flanked fragments;
      (ii) a plurality of partially double-stranded nucleic acid barcode molecules each comprising:
         (I) a first strand comprising a common barcode sequence, and
         (II) a second strand comprising (A) a 5' overhang sequence, wherein said 5' overhang sequence comprises a noncanonical base and a first sequence complementary to said adapter sequence, and (B) a second sequence complementary to a sequence of said first strand;
   (c) using said adapter-flanked fragment and a first partially double-stranded, said nucleic acid barcode molecule of said plurality of partially double-stranded nucleic acid barcode molecules to generate a barcoded nucleic acid molecule comprising a sequence of said adapter-flanked fragment and said common barcode sequence; and
   (d) subjecting a second partially double-stranded nucleic acid barcode molecule of said plurality of partially double-stranded nucleic acid barcode molecules to nucleic acid extension conditions comprising a polymerase, wherein said noncanonical base or a derivative thereof in said second partially double-stranded nucleic acid barcode molecule inhibits full extension of said first strand of said second partially double-stranded nucleic acid barcode molecule.

2. The method of claim 1, wherein said second strand further comprises a blocking group.

3. The method of claim 2, wherein said blocking group is a 3' blocking group.

4. The method of claim 3, wherein said 3' blocking group is a 2'-3'-dideoxycytosine (ddC), a 2'-5' linked nucleoside, a 3' C3 spacer, an amino-modified C6, an inverted deoxythymidine (dT), a 3' amino modified nucleotide, or a 3' phosphate group.

5. The method of claim 4, wherein said 2'-5' linked nucleoside is a 3'-deoxythymidine (3'-dT), a 3'-deoxycytidine (3'-dC), a 3'-deoxyadenosine (3'-dA), or a 3'-deoxyguanosine (3'-dG).

6. The method of claim 1, wherein said noncanonical base is uracil.

7. The method of claim 1, further comprising, subsequent to (c), generating said derivative of said noncanonical base, wherein said derivative is an abasic site, in said second strand at a position of said noncanonical base.

8. The method of claim 7, wherein said noncanonical base is uracil and wherein said abasic site is generated using a uracil-DNA-glycosylase (UDG).

9. The method of claim 1, further comprising, subsequent to (c), pooling contents of said plurality of partitions to yield pooled contents, processing said pooled contents to generate an abasic site at a position of said noncanonical base, and performing one or more nucleic acid reactions on said barcoded nucleic acid molecule or a derivative thereof to generate a reaction product, wherein said processing reduces barcode exchange in said reaction product.

10. The method of claim 9, wherein said noncanonical base is uracil and wherein said processing comprises using an enzyme to generate said abasic site.

11. The method of claim 10, wherein said enzyme is uracil-DNA-glycosylase (UDG).

12. The method of claim 9, wherein said one or more nucleic acid reactions comprises one or more nucleic acid amplification reactions.

13. The method of claim 1, wherein (c) comprises ligating said adapter-flanked fragment to said first partially double-stranded nucleic acid barcode molecule to generate said barcoded nucleic acid molecule.

14. The method of claim 1, wherein said adapter-flanked fragment in (b) comprises a first adapter sequence and a second adapter sequence, wherein said plurality of transposase complexes comprises a plurality of transposase molecules, and wherein said sequence of said adapter-flanked fragment in (c) comprises said first adapter sequence and said second adapter sequence.

15. The method of claim 1, wherein said plurality of partitions is a plurality of droplets in an emulsion.

16. The method of claim 1, wherein said plurality of partitions comprises at least 1,000 microwells.

17. The method of claim 1, wherein said plurality of partially double-stranded nucleic acid barcode molecules is attached to a bead.

18. The method of claim 17, wherein said plurality of partially double-stranded nucleic acid barcode molecules is releasable from said bead upon application of a stimulus.

19. The method of claim 17, wherein said bead is a gel bead.

20. The method of claim 19, wherein said gel bead is degradable upon application of a stimulus.

21. The method of claim 1, further comprising permeabilizing said plurality of biological particles before (a).

22. The method of claim 21, wherein said transposase complexes comprise Tn5 transposase.

23. The method of claim 22, wherein said biological particle is subjected to a condition to release said adapter-flanked fragment from said biological particle before (c).

24. The method of claim 22, further comprising amplifying said barcoded nucleic acid molecule to generate amplified products.

25. The method of claim 24, further comprising determining sequences of said amplified products.

26. The method of claim 25, further comprising analyzing said sequences of said amplified product to determine areas of accessible chromatin in said biological particle.

27. The method of claim 1, wherein (c) comprises performing linear amplification on said adapter-flanked fragment using said first partially double-stranded nucleic acid barcode molecule as a primer.

28. The method of claim 1, further comprising amplifying said barcoded nucleic acid molecule to generate amplified products.

29. The method of claim 28, further comprising determining sequences of said amplified products.

30. The method of claim 29, further comprising analyzing said sequences of said amplified products to determine areas of accessible chromatin in said biological particle.

\* \* \* \* \*

SEQUENCE LISTING

<160> NUMBER OF SEQ ID NOS: 9

<210> SEQ ID NO 1
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
aatgatacgg cgaccaccga gatctacacg actagtgtac ccacgtcgtc ggcagcgtca    60
gatgtgtata agagacagat gggtagctct caccatcatc atcatcactc tagcggtctg   120
gtccctcgcg gtagccacat gccacgtaaa atgtatagct gtgattttga gactacgacg   180
aaagttgaag attgccgtgt gtgggcgtat ggttacatga atattgaaga tcactccgag   240
tataagattg gcaatagcct ggatgaattc atggcgtgct gtctcttata cacatctccg   300
agcccacgag ac                                                       312
```

<210> SEQ ID NO 2
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
aatgatacgg cgaccaccga gatctacaca tctgaagaca tcgtctcgtc ggcagcgtca    60
gatgtgtata agagacagat gggtagctct caccatcatc atcatcactc tagcggtctg   120
gtccctcgcg gtagccacat gccacgtaaa atgtatagct gtgattttga gactacgacg   180
aaagttgaag attgccgtgt gtgggcgtat ggttacatga atattgaaga tcactccgag   240
tataagattg gcaatagcct ggatgaattc atggcgtgct gtctcttata cacatctccg   300
agcccacgag ac                                                       312
```

<210> SEQ ID NO 3
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
aatgatacgg cgaccaccga gatctacact cagcgtcttc catgatcgtc ggcagcgtca    60
gatgtgtata agagacagat gggtagctct caccatcatc atcatcactc tagcggtctg   120
gtccctcgcg gtagccacat gccacgtaaa atgtatagct gtgattttga gactacgacg   180
aaagttgaag attgccgtgt gtgggcgtat ggttacatga atattgaaga tcactccgag   240
tataagattg gcaatagcct ggatgaattc atggcgtgct gtctcttata cacatctccg   300
agcccacgag ac                                                       312
```

<210> SEQ ID NO 4
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
aatgatacgg cgaccaccga gatctacacc gtatcctcag gtcagtcgtc ggcagcgtca    60
gatgtgtata agagacagat gggtagctct caccatcatc atcatcactc tagcggtctg   120
gtccctcgcg gtagccacat gccacgtaaa atgtatagct gtgattttga gactacgacg   180
aaagttgaag attgccgtgt gtgggcgtat ggttacatga atattgaaga tcactccgag   240
```
tataagattg gcaatagcct ggatgaattc atggcgtgct gtctcttata cacatctccg    300
agcccacgag ac    312

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aatgatacgg cgaccaccga gatctacacg agcatgaggt agact    45

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gacgctgccg acgaagtcta cctcatgctc gtgtagatct cggtggtcgc cgtatcatt    59

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
gacgctgccu acgaagtcta cctcatgctc gtgtagatct cggtggtcgc cgtatcatt    59

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Abasic nucleotide

<400> SEQUENCE: 8
gacgctgccn acgaagtcta cctcatgctc gtgtagatct cggtggtcgc cgtatcatt    59

<210> SEQ ID NO 9
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(36)
<223> OTHER INFORMATION: a, c, t, g, unknown or other
<220> FEATURE:

```
<221> NAME/KEY: modified_base
<222> LOCATION: (39)..(45)
<223> OTHER INFORMATION: a, c, t, g, unknown or other

<400> SEQUENCE: 9
aatgatacgg cgaccaccga gatctacacn nnnnnngtnn nnnnntcgtc ggcagcgtca      60
gatgtgtata agagacaa                                                   78
```